United States Patent
Lee et al.

(10) Patent No.: US 9,587,255 B2
(45) Date of Patent: Mar. 7, 2017

(54) 3-HYDROXYPROPIONIC ACID-PRODUCING RECOMBINANT MICROORGANISM AND METHOD OF PRODUCING 3-HYDROXYPROPIONIC ACID USING THE SAME

(71) Applicant: Samsung Electronics Co., Ltd., Suwon-si, Gyeonggi-do (KR)

(72) Inventors: Chanmoo Lee, Gwacheon-si (KR); Youngsoo Kim, Seoul (KR); In Suk Choi, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 235 days.

(21) Appl. No.: 14/411,845

(22) PCT Filed: Jul. 1, 2013

(86) PCT No.: PCT/KR2013/005803
§ 371 (c)(1),
(2) Date: Dec. 29, 2014

(87) PCT Pub. No.: WO2014/003502
PCT Pub. Date: Jan. 3, 2014

(65) Prior Publication Data
US 2015/0240269 A1    Aug. 27, 2015

(30) Foreign Application Priority Data

Jun. 29, 2012 (KR) ........................ 10-2012-0071367

(51) Int. Cl.
| C12P 7/42 | (2006.01) |
| C12N 9/00 | (2006.01) |
| C12N 9/88 | (2006.01) |
| C12N 9/02 | (2006.01) |

(52) U.S. Cl.
CPC .............. *C12P 7/42* (2013.01); *C12N 9/0008* (2013.01); *C12N 9/88* (2013.01); *C12Y 102/01003* (2013.01); *C12Y 402/0103* (2013.01); *Y02P 20/52* (2015.11)

(58) Field of Classification Search
None
See application file for complete search history.

(56) References Cited

U.S. PATENT DOCUMENTS

| 5,686,276 | A | 11/1997 | Laffend et al. |
| 6,025,184 | A | 2/2000 | Laffend et al. |
| 6,428,767 | B1 | 8/2002 | Burch et al. |
| 7,135,309 | B1 | 11/2006 | Laffend et al. |
| 7,169,588 | B2 | 1/2007 | Burch et al. |
| 7,629,161 | B2 | 12/2009 | Laffend et al. |
| 2012/0270287 | A1 | 10/2012 | Kim et al. |

FOREIGN PATENT DOCUMENTS

| KR | 2004-0071157 A | 8/2004 |
| KR | 2010-0134545 A | 12/2010 |
| KR | 2010-1048485 B1 | 2/2011 |
| WO | 2011/052819 A1 | 5/2011 |

OTHER PUBLICATIONS

Raj et al., "Production of 3-hydroxypropionic acid from glycerol by a novel recombinant *Escherichia coli* BL21 strain", *Process Biochemistry*, 43: 1440-1446 (2008).
GenBank Accession Record No. CP002281.1 (submission includes only the first page of the database entry), submitted on Nov. 21, 2011.
GenBank Accession Record No. YP_003967422.1, submitted on Jun. 18, 2012.
Korean Patent Office, International Search Report issued in International Patent Application No. PCT/KR2013/005803, pp. 1-3 (Oct. 29, 2013).

*Primary Examiner* — Suzanne M Noakes
*Assistant Examiner* — Jae W Lee
(74) *Attorney, Agent, or Firm* — Leydig, Voit & Mayer, Ltd.

(57) ABSTRACT

Disclosed is a method of producing 3-hydroxypropionic acid comprising the step of culturing recombinant microorganism comprising a nucleic acid sequence encoding *Ilyobacter polytropus*-derived glycerol dehydratase, and a nucleic acid sequence encoding dehydrogenase, which converts 3-hydroxypropionaldehyde into 3-hydroxypropionic acid, and a recombinant microorganism used therefor. According to the present invention, the production of 3-hydroxypropionic acid remarkably increases and the production amount of 1,3-propanediol (1,3-PDO), which is generated as by-products when producing 3-hydroxypropionic acid, remarkably decreases, compared to known recombinant microorganisms comprising gene expressing *Klebsiella pneumonia*-derived Vitamin $B_{12}$-dependent glycerol dehydratase.

19 Claims, 14 Drawing Sheets

ET - iBAB - H

SEQUENCE LISTING

```
<160> NUMBER OF SEQ ID NOS: 25

<210> SEQ ID NO 1
<211> LENGTH: 1665
<212> TYPE: DNA
<213> ORGANISM: Ilyobacter polytropus

<400> SEQUENCE: 1
atgaaatcaa aaagatttga agtattgaag gaacgtcctg taaataaaga tggctttata      60
agtgaatgga tagaagaagg actaatcgca atggaaagtc ctaacgatcc taatccaagt     120
ttgaaaatag aaaatggtca aataacagag ttagacggta aaagcagaga agaatttgac     180
```

```
atgatcgaca gatttatagc agattatgca ataaatatgg aaaatgctga aaaagctatg    240
aaaatgtcat ctatggaaat atctaaaaaa ctagtagaca taaatgtatc aagagatgaa    300
gtgctggaaa taacaacagg aattacccca gcaaaaataa ttaaagttat ggaacacatg    360
aatgttgtag agatgatgat ggccgtacaa aaaatgagag ccagaaaaac tccttccaat    420
cagtgtcatg taactaactt gagagacaat cctgtattaa ttgccgctga tgctgccgaa    480
gcgtcagtaa gaggttttga tgaacaggag actacaatcg gtatagtaag atatgcacct    540
ttcaatgcca tctcaatatt tgtaggttca caagtaggta gaggaggaat actgactcag    600
tgttctgtag aagaagctac tgaattagag cttggaatga aaggattcac aagttatgca    660
gaaacagtgt ctgtatatgg tacagagcaa gtgtttatag acggtgacga cactccttgg    720
tcaaaagcct tccttgcttc agcatatgca tcaagaggat taaaaatgag atttacatct    780
ggaactggtt cagaggctct tatgggaaat gctgaaggga atcaatgct ttaccttgaa     840 gcaagatgta tctacgtaac aagagggtct ggagtacaag gactacaaaa tggttctgta    900
agctgcatag ggatgcctgg gtcactacct ggaggaataa gggctgtact ggctgaaaac    960
ctgatagcaa tgttacttga cttagaatgt gcatcagcaa atgaccagac attctctcac   1020
tcagaatata aaggacagc aagaactcta atgcagatgc ttcctggaac agacttcata    1080
ttctcaggat atagtgccgt accaaactgt gataacatgt tgctggatc aaattttgat    1140 gcagaggatt tgatgactaa taatgctctt cagagagacc ttaaaataga cggtggttta   1200
aaacctgtaa ctgaagatga gattgtcaaa gtaagaaata aagcagccag agcaatacag   1260
gggttattca agaacttga tcttcctgaa ataacgatg aagaagtgga agcagcaaca    1320
tatgcccacg gaagtgttga tatgcctgca agaaatgtgg ttgaagattt aaaagcggca   1380
gaagaacttt taagctctgg aataacagga gtagatcttg ttaaaggact agcagaagc    1440 ggatttgacg atgtagctga gcatgtttta ggtatgttaa acagagagt ttcaggagat    1500 tacctgcaaa cttcagctat attagacaaa ggctttaaaa taaagagtgc cataaacgat   1560
agaaatgatt acatgggtcc tggaagcgga tatagaataa gcgaggaaag atgggaagag   1620
atcaaaaata tcccatcagc tataaaacca gaaagtatag aatag                   1665
```

<210> SEQ ID NO 2
<211> LENGTH: 554
<212> TYPE: PRT
<213> ORGANISM: Ilyobacter polytropus

<400> SEQUENCE: 2

```
Met Lys Ser Lys Arg Phe Glu Val Leu Lys Glu Arg Pro Val Asn Lys
 1               5                  10                  15

Asp Gly Phe Ile Ser Glu Trp Ile Glu Glu Gly Leu Ile Ala Met Glu
            20                  25                  30

Ser Pro Asn Asp Pro Asn Pro Ser Leu Lys Ile Glu Asn Gly Gln Ile
        35                  40                  45

Thr Glu Leu Asp Gly Lys Ser Arg Glu Glu Phe Asp Met Ile Asp Arg
    50                  55                  60

Phe Ile Ala Asp Tyr Ala Ile Asn Met Glu Asn Ala Glu Lys Ala Met
65                  70                  75                  80

Lys Met Ser Ser Met Glu Ile Ser Lys Lys Leu Val Asp Ile Asn Val
                85                  90                  95

Ser Arg Asp Glu Val Leu Glu Ile Thr Thr Gly Ile Thr Pro Ala Lys
            100                 105                 110
```

```
Ile Ile Lys Val Met Glu His Met Asn Val Val Glu Met Met Ala
        115                 120                 125
Val Gln Lys Met Arg Ala Arg Lys Thr Pro Ser Asn Gln Cys His Val
        130                 135                 140
Thr Asn Leu Arg Asp Asn Pro Val Leu Ile Ala Ala Asp Ala Ala Glu
145                 150                 155                 160
Ala Ser Val Arg Gly Phe Asp Glu Gln Glu Thr Thr Ile Gly Ile Val
                165                 170                 175
Arg Tyr Ala Pro Phe Asn Ala Ile Ser Ile Phe Val Gly Ser Gln Val
            180                 185                 190
Gly Arg Gly Gly Ile Leu Thr Gln Cys Ser Val Glu Glu Ala Thr Glu
        195                 200                 205
Leu Glu Leu Gly Met Lys Gly Phe Thr Ser Tyr Ala Glu Thr Val Ser
210                 215                 220
Val Tyr Gly Thr Glu Gln Val Phe Ile Asp Gly Asp Thr Pro Trp
225                 230                 235                 240
Ser Lys Ala Phe Leu Ala Ser Ala Tyr Ala Ser Arg Gly Leu Lys Met
                245                 250                 255
Arg Phe Thr Ser Gly Thr Gly Ser Glu Ala Leu Met Gly Asn Ala Glu
            260                 265                 270
Gly Lys Ser Met Leu Tyr Leu Glu Ala Arg Cys Ile Tyr Val Thr Arg
        275                 280                 285
Gly Ser Gly Val Gln Gly Leu Gln Asn Gly Ser Val Ser Cys Ile Gly
        290                 295                 300
Met Pro Gly Ser Leu Pro Gly Gly Ile Arg Ala Val Leu Ala Glu Asn
305                 310                 315                 320
Leu Ile Ala Met Leu Leu Asp Leu Glu Cys Ala Ser Ala Asn Asp Gln
                325                 330                 335
Thr Phe Ser His Ser Glu Tyr Arg Arg Thr Ala Arg Thr Leu Met Gln
            340                 345                 350
Met Leu Pro Gly Thr Asp Phe Ile Phe Ser Gly Tyr Ser Ala Val Pro
        355                 360                 365
Asn Cys Asp Asn Met Phe Ala Gly Ser Asn Phe Asp Ala Glu Asp Phe
370                 375                 380
Asp Asp Tyr Asn Ala Leu Gln Arg Asp Leu Lys Ile Asp Gly Gly Leu
385                 390                 395                 400
Lys Pro Val Thr Glu Asp Ile Val Lys Val Arg Asn Lys Ala Ala
                405                 410                 415
Arg Ala Ile Gln Gly Leu Phe Lys Glu Leu Asp Leu Pro Glu Ile Thr
            420                 425                 430
Asp Glu Glu Val Glu Ala Ala Thr Tyr Ala His Gly Ser Val Asp Met
        435                 440                 445
Pro Ala Arg Asn Val Val Glu Asp Leu Lys Ala Ala Glu Glu Leu Leu
450                 455                 460
Ser Ser Gly Ile Thr Gly Val Asp Leu Val Lys Gly Leu Ser Arg Ser
465                 470                 475                 480
Gly Phe Asp Asp Val Ala Glu His Val Leu Gly Met Leu Lys Gln Arg
                485                 490                 495
Val Ser Gly Asp Tyr Leu Gln Thr Ser Ala Ile Leu Asp Lys Gly Phe
            500                 505                 510
Lys Ile Lys Ser Ala Ile Asn Asp Arg Asn Asp Tyr Met Gly Pro Gly
        515                 520                 525
Ser Gly Tyr Arg Ile Ser Glu Glu Arg Trp Glu Glu Ile Lys Asn Ile
```

```
                530                 535                 540
Pro Ser Ala Ile Lys Pro Glu Ser Ile Glu
545                 550

<210> SEQ ID NO 3
<211> LENGTH: 564
<212> TYPE: DNA
<213> ORGANISM: Ilyobacter polytropus

<400> SEQUENCE: 3
atggaaaata aatttgtacc atctgtaaag atagaagaaa tcggagaagc aaaaaaagga      60
agcagatctg aagaagtagt tataggactg gctcctgcat ttaaaaaatt tcaacataaa     120
acaataacag atgtccctca cgatgaagtc ctgactgaac ttatcgcagg tatagaggaa     180
gagggattaa aggcaagaat cgtaagagta acaagaactt ctgatgtttc atttatggcg     240
ctggatgctg caaagttaag tggttctgga ataggaatag gaattcagtc aaagggaaca     300
acagtaatcc accaaaagga tctgcttcct ctaaacaatc tagaactttt cccacaggct     360
ccactattaa cacctgaaac attcagatta ataggaaaaa atgctgcaaa atatgcaaag     420
ggagaatctc caaatccagt acctgtagcc agtgaccaga tggcgagacc taaatatcag     480
gcaaaagcag cattactaca tataaaagag acaaaacatg tcgttcaaca cggaaaacca     540
gtagagataa agtatgaatt ttag                                            564

<210> SEQ ID NO 4
<211> LENGTH: 210
<212> TYPE: PRT
<213> ORGANISM: Ilyobacter polytropus

<400> SEQUENCE: 4

Met Gly Arg Asp Gln Lys Tyr Pro Ile Ser Tyr Lys Thr Arg Lys Tyr
1               5                   10                  15

Arg Ile Gly Glu Phe Thr Ile Met Glu Asn Lys Phe Val Pro Ser Val
            20                  25                  30

Lys Ile Glu Glu Ile Gly Glu Ala Lys Lys Gly Ser Arg Ser Glu Glu
        35                  40                  45

Val Val Ile Gly Leu Ala Pro Ala Phe Lys Lys Phe Gln His Lys Thr
    50                  55                  60

Ile Thr Asp Val Pro His Asp Glu Val Leu Thr Glu Leu Ile Ala Gly
65                  70                  75                  80

Ile Glu Glu Glu Gly Leu Lys Ala Arg Ile Val Arg Val Thr Arg Thr
                85                  90                  95

Ser Asp Val Ser Phe Met Ala Leu Asp Ala Ala Lys Leu Ser Gly Ser
            100                 105                 110

Gly Ile Gly Ile Gly Ile Gln Ser Lys Gly Thr Thr Val Ile His Gln
        115                 120                 125

Lys Asp Leu Leu Pro Leu Asn Asn Leu Glu Leu Phe Pro Gln Ala Pro
    130                 135                 140

Leu Leu Thr Pro Glu Thr Phe Arg Leu Ile Gly Lys Asn Ala Ala Lys
145                 150                 155                 160

Tyr Ala Lys Gly Glu Ser Pro Asn Pro Val Pro Val Ala Ser Asp Gln
                165                 170                 175

Met Ala Arg Pro Lys Tyr Gln Ala Lys Ala Ala Leu Leu His Ile Lys
            180                 185                 190

Glu Thr Lys His Val Val Gln His Gly Lys Pro Val Glu Ile Lys Tyr
        195                 200                 205
```

Glu Phe
    210

<210> SEQ ID NO 5
<211> LENGTH: 432
<212> TYPE: DNA
<213> ORGANISM: Ilyobacter polytropus

<400> SEQUENCE: 5

```
atgaatatag atgttaaaaa tataaatcca atctctgatt atccattagg agaaaagaga      60
aaagaatggt tgaaaacatc cacaggtaaa actttggatg aaataacttt agaaaatgta     120
ataaatggag atataaagcc tgaagatata agaatctcac ctgaaactct aaaattacag     180
ggagagatag caaagaaagg taacaggcca actataacaa agaactttga agagccagt     240
gaaatggttg ccattccaga tgataaaata ttagcaactt acaacgcttt gagaccttac     300
agatcttcaa aggaagaatt atttgaaata gccgatgaac tagaaagtaa gtattcagct     360
gttgtaatat ctgcatttat caaggaagcc gcagaagttt atgaacaaag aggtcaactt     420
agaaaagatt ag                                                         432
```

<210> SEQ ID NO 6
<211> LENGTH: 143
<212> TYPE: PRT
<213> ORGANISM: Ilyobacter polytropus

<400> SEQUENCE: 6

Met Asn Ile Asp Val Lys Asn Ile Asn Pro Ile Ser Asp Tyr Pro Leu
  1               5                  10                  15

Gly Glu Lys Arg Lys Glu Trp Leu Lys Thr Ser Thr Gly Lys Thr Leu
             20                  25                  30

Asp Glu Ile Thr Leu Glu Asn Val Ile Asn Gly Asp Ile Lys Pro Glu
         35                  40                  45

Asp Ile Arg Ile Ser Pro Glu Thr Leu Lys Leu Gln Gly Glu Ile Ala
     50                  55                  60

Lys Lys Gly Asn Arg Pro Thr Ile Thr Lys Asn Phe Glu Arg Ala Ser
 65                  70                  75                  80

Glu Met Val Ala Ile Pro Asp Asp Lys Ile Leu Ala Thr Tyr Asn Ala
                 85                  90                  95

Leu Arg Pro Tyr Arg Ser Ser Lys Glu Glu Leu Phe Glu Ile Ala Asp
            100                 105                 110

Glu Leu Glu Ser Lys Tyr Ser Ala Val Val Ile Ser Ala Phe Ile Lys
        115                 120                 125

Glu Ala Ala Glu Val Tyr Glu Gln Arg Gly Gln Leu Arg Lys Asp
    130                 135                 140

<210> SEQ ID NO 7
<211> LENGTH: 1824
<212> TYPE: DNA
<213> ORGANISM: Ilyobacter polytropus

<400> SEQUENCE: 7

```
atgaagatca tagtgggtgt agatattgga aatgctacaa cagaagtagc tttggcaaag      60
gtagacaata tagaatgtaa gttttatcc agtgccttac atgaaacaac aggttttaaaa     120
ggtactaaag ataatgtttt gggaataaaa agagccatta gaaggcaat gaaaagagct     180
gatttaaaaa atgcagattt atctttaatc aggataaatg aagctactcc tgttatagga     240
```

```
gacgtttcta tggaaactat aacagaaaca ataattacag agtctactat gattggacat    300
aacccttcaa ctcctggggg aataggtctt gggataggag aaacaatcct attccaagag    360
cttggaaatt ttgaaaatga taaagattac atagtaatag tggaaaaaag tttcagcttc    420
ttagaggtag ctcacagaat caatgaagct tttaaaaatg gatgcaaaat aaagggtgct    480
attattcaaa aagatgatgg ggttctcata ataacagac tcataaataa aatccccata     540
gttgatgagg tacttttgt taaaaaagta cctacaggga tgaaggctgc tgtagaagta     600
gctccacagg gaaaaataat agaggttatt tcaaatccat atggcattgc cacaattttt    660
tccctcactt cagaagagac taaaaaaata gttcctattt ctaaagcact tataggcaac    720
aggtctggag tagttatcaa gacacctcac ggagatgtaa aagagaaggt tatccctgct    780
ggaaggatac agattgacgg aaactacagg tcaaaaagtg taaatataga agagggttcc    840
aaaagaataa tgaaagccct gggaagtatt gagcatgtcc aagatataaa tggagaatct    900
ggaaccaata tcggaggaat gctaaaaaat gtaaaaagtg taatgggaa tttcaccaat    960 gagtccattg ataatataaa aataaaagac atattggcag tagataccctt tgtcccacaa   1020 aagataaagg ggggaattgc agaagaattt gtatttgaaa atgctgtagg aatagctgca   1080
atggtaaata ccaaaaaaaa tcaaatgtcc gaagtagcga aagagattga aaaagaactg   1140
ggagtaaaag tagaagtagg aggagtagag gcagatatgg ctataaccgg tgctctaact   1200
actccaggca caggaacacc tctggtaatt gtagatatag gagcaggttc gacagatgca   1260
tgttccattg acagatatgg aaataaagaa ctggttcatc tggccggagc tggtaatatg   1320
acaacacttc ttattcaaaa agagctgggt atagaggatt ttaatcttgc tgaagatata   1380
aaaaaatatc ctctggcaaa agtagaatct ctattttata taagacacga ggatggaaat   1440
gttcaatttt ttgaaaactc tctttctccg aaagtatttg ctaaaaatgt ccttataaaa   1500
gaaggtgaac ttattccaat cgaccttgat atgtctctgg aaaaaatcag aattatcaga   1560
aggtctgcca aaagaaaaat ttttataacc aatgtactta gatcattaag gaaagtttct   1620
catacaaaaa atattaggga ttttgaattt gtagttattg ttggaggatc tgcattggat   1680
tttgaaatat ctcagatgat aactgaagct ttatctgagt atggaatagt agcaggatgc   1740
ggaaatataa gaggaacaga gggccctaga aatgctgtag ccactggact tgtaatgggg   1800
gtgaatgatg gacaacaggc ctaa                                          1824
```

<210> SEQ ID NO 8
<211> LENGTH: 607
<212> TYPE: PRT
<213> ORGANISM: Ilyobacter polytropus

<400> SEQUENCE: 8

```
Met Lys Ile Ile Val Gly Val Asp Ile Gly Asn Ala Thr Thr Glu Val
  1               5                  10                  15

Ala Leu Ala Lys Val Asp Asn Ile Glu Cys Lys Phe Leu Ser Ser Ala
                 20                  25                  30

Leu His Glu Thr Thr Gly Leu Lys Gly Thr Lys Asp Asn Val Leu Gly
             35                  40                  45

Ile Lys Arg Ala Ile Lys Lys Ala Met Lys Arg Ala Asp Leu Lys Asn
         50                  55                  60

Ala Asp Leu Ser Leu Ile Arg Ile Asn Glu Ala Thr Pro Val Ile Gly
 65                  70                  75                  80

Asp Val Ser Met Glu Thr Ile Thr Glu Thr Ile Ile Thr Glu Ser Thr
                 85                  90                  95
```

```
Met Ile Gly His Asn Pro Ser Thr Pro Gly Ile Gly Leu Gly Ile
            100                 105                 110

Gly Glu Thr Ile Leu Phe Gln Glu Leu Gly Asn Phe Glu Asn Asp Lys
            115                 120                 125

Asp Tyr Ile Val Ile Val Glu Lys Ser Phe Ser Phe Leu Glu Val Ala
130                 135                 140

His Arg Ile Asn Glu Ala Phe Lys Asn Gly Cys Lys Ile Lys Gly Ala
145                 150                 155                 160

Ile Ile Gln Lys Asp Asp Gly Val Leu Ile Asn Asn Arg Leu Ile Asn
            165                 170                 175

Lys Ile Pro Ile Val Asp Glu Val Leu Phe Val Lys Lys Val Pro Thr
            180                 185                 190

Gly Met Lys Ala Ala Val Glu Val Ala Pro Gln Gly Lys Ile Ile Glu
            195                 200                 205

Val Ile Ser Asn Pro Tyr Gly Ile Ala Thr Ile Phe Ser Leu Thr Ser
210                 215                 220

Glu Glu Thr Lys Lys Ile Val Pro Ile Ser Lys Ala Leu Ile Gly Asn
225                 230                 235                 240

Arg Ser Gly Val Val Ile Lys Thr Pro His Gly Asp Val Lys Glu Lys
            245                 250                 255

Val Ile Pro Ala Gly Arg Ile Gln Ile Asp Gly Asn Tyr Arg Ser Lys
            260                 265                 270

Ser Val Asn Ile Glu Glu Gly Ser Lys Arg Ile Met Lys Ala Leu Gly
            275                 280                 285

Ser Ile Glu His Val Gln Asp Ile Asn Gly Glu Ser Gly Thr Asn Ile
            290                 295                 300

Gly Gly Met Leu Lys Asn Val Lys Ser Val Met Gly Asn Phe Thr Asn
305                 310                 315                 320

Glu Ser Ile Asp Asn Ile Lys Ile Lys Asp Ile Leu Ala Val Asp Thr
            325                 330                 335

Phe Val Pro Gln Lys Ile Lys Gly Gly Ile Ala Glu Glu Phe Val Phe
            340                 345                 350

Glu Asn Ala Val Gly Ile Ala Ala Met Val Asn Thr Lys Lys Asn Gln
            355                 360                 365

Met Ser Glu Val Ala Lys Glu Ile Glu Lys Glu Leu Gly Val Lys Val
370                 375                 380

Glu Val Gly Gly Val Glu Ala Asp Met Ala Ile Thr Gly Ala Leu Thr
385                 390                 395                 400

Thr Pro Gly Thr Gly Thr Pro Leu Val Ile Val Asp Ile Gly Ala Gly
            405                 410                 415

Ser Thr Asp Ala Cys Ser Ile Ser Arg Tyr Gly Asn Lys Glu Leu Val
            420                 425                 430

His Leu Ala Gly Ala Gly Asn Met Thr Thr Leu Leu Ile Gln Lys Glu
            435                 440                 445

Leu Gly Ile Glu Asp Phe Asn Leu Ala Glu Asp Ile Lys Lys Tyr Pro
            450                 455                 460

Leu Ala Lys Val Glu Ser Leu Phe Tyr Ile Arg His Glu Asp Gly Asn
465                 470                 475                 480

Val Gln Phe Phe Glu Asn Ser Leu Ser Pro Lys Val Phe Ala Lys Asn
            485                 490                 495

Val Leu Ile Lys Glu Gly Glu Leu Ile Pro Ile Asp Leu Asp Met Ser
            500                 505                 510
```

Leu Glu Lys Ile Arg Ile Ile Arg Arg Ser Ala Lys Arg Lys Ile Phe
            515                 520                 525

Ile Thr Asn Val Leu Arg Ser Leu Arg Lys Val Ser His Thr Lys Asn
    530                 535                 540

Ile Arg Asp Phe Glu Phe Val Val Ile Val Gly Gly Ser Ala Leu Asp
545                 550                 555                 560

Phe Glu Ile Ser Gln Met Ile Thr Glu Ala Leu Ser Glu Tyr Gly Ile
                565                 570                 575

Val Ala Gly Cys Gly Asn Ile Arg Gly Thr Gly Pro Arg Asn Ala
            580                 585                 590

Val Ala Thr Gly Leu Val Met Gly Val Asn Asp Gly Gln Gln Ala
            595                 600                 605

<210> SEQ ID NO 9
<211> LENGTH: 324
<212> TYPE: DNA
<213> ORGANISM: Ilyobacter polytropus

<400> SEQUENCE: 9
atggacaaca ggcctaatat aacattattt tgctcagata atattgacag ggaatatatt      60
aatgaaattt tgtggggtat agaggaggaa gagataccat atcttctgaa aattgtacct     120
tctaaagaag ttgtcaaaga aaattatgtt tcaggaactc tagagatagg tatcggagta     180
ttagaaaatg gcgacgccct tctaacaaca aggaagtacg ataaggaata tatacaaaag     240
gcaaacattt ttgtagaaaa aaataaattg agagatttag gaagcaacgg agcaagactt     300
gtaaagggtc tgccacttag ataa                                           324

<210> SEQ ID NO 10
<211> LENGTH: 108
<212> TYPE: PRT
<213> ORGANISM: Ilyobacter polytropus

<400> SEQUENCE: 10

Met Met Asp Asn Arg Pro Asn Ile Thr Leu Phe Cys Ser Asp Asn Ile
1               5                   10                  15

Asp Arg Glu Tyr Ile Asn Glu Ile Leu Trp Gly Ile Glu Glu Glu
            20                  25                  30

Ile Pro Tyr Leu Leu Lys Ile Val Pro Ser Lys Glu Val Val Lys Glu
        35                  40                  45

Asn Tyr Val Ser Gly Thr Leu Glu Ile Gly Ile Gly Val Leu Glu Asn
    50                  55                  60

Gly Asp Ala Leu Leu Thr Thr Arg Lys Tyr Asp Lys Glu Tyr Ile Gln
65                  70                  75                  80

Lys Ala Asn Ile Phe Val Glu Lys Asn Lys Leu Arg Asp Leu Gly Ser
                85                  90                  95

Asn Gly Ala Arg Leu Val Lys Gly Leu Pro Leu Arg
            100                 105

<210> SEQ ID NO 11
<211> LENGTH: 1488
<212> TYPE: DNA
<213> ORGANISM: Escherichia coli
<220> FEATURE:
<221> NAME/KEY: MISC_FEATURE
<222> LOCATION: (1)..(1488)
<223> OTHER INFORMATION: K-12

<400> SEQUENCE: 11

```
atgaattttc atcatctggc ttactggcag ataaagcgt taagtctcgc cattgaaaac    60
cgcttattta ttaacggtga atatactgct gcggcggaaa atgaaacctt tgaaaccgtt   120
gatccggtca cccaggcacc gctggcgaaa attgcccgcg gcaagagcgt cgatatcgac   180
cgtgcgatga gcgcagcacg cggcgtattt gaacgcggcg actggtcact ctcttctccg   240
gctaaacgta aagcggtact gaataaactc gccgatttaa tggaagccca cgccgaagag   300
ctggcactgc tggaaactct cgacaccggc aaaccgattc gtcacagtct gcgtgatgat   360
attcccggcg cggcgcgcgc cattcgctgg tacgccgaag cgatcgacaa agtgtatggc   420
gaagtggcga ccaccagtag ccatgagctg gcgatgatcg tgcgtgaacc ggtcggcgtg   480
attgccgcca tcgtgccgtg gaacttcccg ctgttgctga cttgctggaa actcggcccg   540
gcgctggcgg cgggaaacag cgtgattcta aaaccgtctg aaaaatcacc gctcagtgcg   600
attcgtctcg cggggctggc gaaagaagca ggcttgccgg atggtgtgtt gaacgtggtg   660
acgggttttg gtcatgaagc cgggcaggcg ctgtcgcgtc ataacgatat cgacgccatt   720
gcctttaccg gttcaacccg taccgggaaa cagctgctga agatgcgggc gacagcaac   780
atgaaacgcg tctggctgga agcgggcggc aaaagcgcca catcgttttt cgctgactgc   840
ccggatttgc aacaggcggc aagcgccacc gcagcaggca ttttctacaa ccagggacag   900
gtgtgcatcg ccggaacgcg cctgttgctg aagagagca tcgccgatga attcttagcc   960
ctgttaaaac agcaggcgca aaactggcag ccgggccatc cacttgatcc cgcaaccacc  1020
atgggcacct taatcgactg cgcccacgcc gactcggtcc atagctttat tcgggaaggc  1080
gaaagcaaag gcaactgtt gttggatggc cgtaacgccg gctggctgc cgccatcggc  1140
ccgaccatct tgtggatgt ggacccgaat gcgtccttaa gtcgcgaaga gattttcggt  1200
ccggtgctgg tggtcacgcg tttcacatca gaagaacagg cgctacagct tgccaacgac  1260
agccagtacg gccttggcgc ggcggtatgg acgcgcgacc tctcccgcgc gcaccgcatg  1320
agccgacgcc tgaaagccgg ttccgtcttc gtcaataact acaacgacgg cgatatgacc  1380
gtgccgtttg gcggctataa gcagagcggc aacggtcgcg acaaatccct gcatgccctt  1440
gaaaaattca ctgaactgaa aaccatctgg ataagcctgg aggcctga              1488
```

<210> SEQ ID NO 12
<211> LENGTH: 495
<212> TYPE: PRT
<213> ORGANISM: Escherichia coli
<220> FEATURE:
<221> NAME/KEY: MISC_FEATURE
<222> LOCATION: (1)..(495)
<223> OTHER INFORMATION: K-12

<400> SEQUENCE: 12

Met Asn Phe His His Leu Ala Tyr Trp Gln Asp Lys Ala Leu Ser Leu
 1               5                  10                  15

Ala Ile Glu Asn Arg Leu Phe Ile Asn Gly Glu Tyr Thr Ala Ala Ala
            20                  25                  30

Glu Asn Glu Thr Phe Glu Thr Val Asp Pro Val Thr Gln Ala Pro Leu
        35                  40                  45

Ala Lys Ile Ala Arg Gly Lys Ser Val Asp Ile Asp Arg Ala Met Ser
    50                  55                  60

Ala Ala Arg Gly Val Phe Glu Arg Gly Asp Trp Ser Leu Ser Ser Pro
65                  70                  75                  80

Ala Lys Arg Lys Ala Val Leu Asn Lys Leu Ala Asp Leu Met Glu Ala
                85                  90                  95

His Ala Glu Glu Leu Ala Leu Leu Glu Thr Leu Asp Thr Gly Lys Pro
            100                 105                 110

Ile Arg His Ser Leu Arg Asp Ile Pro Gly Ala Ala Arg Ala Ile
            115                 120                 125

Arg Trp Tyr Ala Glu Ala Ile Asp Lys Val Tyr Gly Glu Val Ala Thr
130                 135                 140

Thr Ser Ser His Glu Leu Ala Met Ile Val Arg Glu Pro Val Gly Val
145                 150                 155                 160

Ile Ala Ala Ile Val Pro Trp Asn Phe Pro Leu Leu Thr Cys Trp
            165                 170                 175

Lys Leu Gly Pro Ala Leu Ala Ala Gly Asn Ser Val Ile Leu Lys Pro
            180                 185                 190

Ser Glu Lys Ser Pro Leu Ser Ala Ile Arg Leu Ala Gly Leu Ala Lys
            195                 200                 205

Glu Ala Gly Leu Pro Asp Gly Val Leu Asn Val Val Thr Gly Phe Gly
            210                 215                 220

His Glu Ala Gly Gln Ala Leu Ser Arg His Asn Asp Ile Asp Ala Ile
225                 230                 235                 240

Ala Phe Thr Gly Ser Thr Arg Thr Gly Lys Gln Leu Leu Lys Asp Ala
            245                 250                 255

Gly Asp Ser Asn Met Lys Arg Val Trp Leu Glu Ala Gly Lys Ser
            260                 265                 270

Ala Asn Ile Val Phe Ala Asp Cys Pro Asp Leu Gln Gln Ala Ala Ser
            275                 280                 285

Ala Thr Ala Ala Gly Ile Phe Tyr Asn Gln Gly Gln Val Cys Ile Ala
            290                 295                 300

Gly Thr Arg Leu Leu Leu Glu Glu Ser Ile Ala Asp Glu Phe Leu Ala
305                 310                 315                 320

Leu Leu Lys Gln Gln Ala Gln Asn Trp Gln Pro Gly His Pro Leu Asp
            325                 330                 335

Pro Ala Thr Thr Met Gly Thr Leu Ile Asp Cys Ala His Ala Asp Ser
            340                 345                 350

Val His Ser Phe Ile Arg Glu Gly Glu Ser Lys Gly Gln Leu Leu Leu
            355                 360                 365

Asp Gly Arg Asn Ala Gly Leu Ala Ala Ala Ile Gly Pro Thr Ile Phe
            370                 375                 380

Val Asp Val Asp Pro Asn Ala Ser Leu Ser Arg Glu Glu Ile Phe Gly
385                 390                 395                 400

Pro Val Leu Val Val Thr Arg Phe Thr Ser Glu Glu Gln Ala Leu Gln
            405                 410                 415

Leu Ala Asn Asp Ser Gln Tyr Gly Leu Gly Ala Ala Val Trp Thr Arg
            420                 425                 430

Asp Leu Ser Arg Ala His Arg Met Ser Arg Arg Leu Lys Ala Gly Ser
            435                 440                 445

Val Phe Val Asn Asn Tyr Asn Asp Gly Asp Met Thr Val Pro Phe Gly
            450                 455                 460

Gly Tyr Lys Gln Ser Gly Asn Gly Arg Asp Lys Ser Leu His Ala Leu
465                 470                 475                 480

Glu Lys Phe Thr Glu Leu Lys Thr Ile Trp Ile Ser Leu Glu Ala
            485                 490                 495

<210> SEQ ID NO 13
<211> LENGTH: 32

```
<212> TYPE: DNA
<213> ORGANISM: Artificial Sequence
<220> FEATURE:
<223> OTHER INFORMATION: Synthetic primer

<400> SEQUENCE: 13
tcatgaaatc aaaaagattt gaagtattga ag                                32

<210> SEQ ID NO 14
<211> LENGTH: 36
<212> TYPE: DNA
<213> ORGANISM: Artificial Sequence
<220> FEATURE:
<223> OTHER INFORMATION: Synthetic primer

<400> SEQUENCE: 14
ggatccctaa tcttttctaa gttgacctct ttgttc                            36

<210> SEQ ID NO 15
<211> LENGTH: 30
<212> TYPE: DNA
<213> ORGANISM: Artificial Sequence
<220> FEATURE:
<223> OTHER INFORMATION: Synthetic primer

<400> SEQUENCE: 15
ggatccaaag gttcggggat agttatgaag                                   30

<210> SEQ ID NO 16
<211> LENGTH: 33
<212> TYPE: DNA
<213> ORGANISM: Artificial Sequence
<220> FEATURE:
<223> OTHER INFORMATION: Synthetic primer

<400> SEQUENCE: 16
gagctcttat ctaagtggca gaccctttac aag                               33

<210> SEQ ID NO 17
<211> LENGTH: 30
<212> TYPE: DNA
<213> ORGANISM: Artificial Sequence
<220> FEATURE:
<223> OTHER INFORMATION: Synthetic primer

<400> SEQUENCE: 17
tttcatatga attttcatca tctggcttac                                   30

<210> SEQ ID NO 18
<211> LENGTH: 30
<212> TYPE: DNA
<213> ORGANISM: Artificial Sequence
<220> FEATURE:
<223> OTHER INFORMATION: Synthetic primer

<400> SEQUENCE: 18
tttagatctt tcggtcattt caggcctcca                                   30

<210> SEQ ID NO 19
<211> LENGTH: 26
<212> TYPE: DNA
<213> ORGANISM: Artificial Sequence
<220> FEATURE:
<223> OTHER INFORMATION: Synthetic primer

<400> SEQUENCE: 19
```

```
atatcatgaa aagatcaaaa cgattt                                          26

<210> SEQ ID NO 20
<211> LENGTH: 29
<212> TYPE: DNA
<213> ORGANISM: Artificial Sequence
<220> FEATURE:
<223> OTHER INFORMATION: Synthetic primer

<400> SEQUENCE: 20
aaagaattcc gcgagcgccc gtttaattc                                       29

<210> SEQ ID NO 21
<211> LENGTH: 30
<212> TYPE: DNA
<213> ORGANISM: Artificial Sequence
<220> FEATURE:
<223> OTHER INFORMATION: Synthetic primer

<400> SEQUENCE: 21
tttgaattct aacgagggga ccgtcatgtc                                      30

<210> SEQ ID NO 22
<211> LENGTH: 30
<212> TYPE: DNA
<213> ORGANISM: Artificial Sequence
<220> FEATURE:
<223> OTHER INFORMATION: Synthetic primer for amplying gdrB. backward

<400> SEQUENCE: 22
atagtcgact cagtttctct cacttaacgg                                      30

<210> SEQ ID NO 23
<211> LENGTH: 2076
<212> TYPE: DNA
<213> ORGANISM: Artificial Sequence
<220> FEATURE:
<223> OTHER INFORMATION: Synthetic aldH2 gene NM_000690.3 (Homo sapiens)

<400> SEQUENCE: 23
attggctgcc gcgcggggcg gggagcgggg tcggctcagt ggccctgaga ccctagctct      60
gctctcggtc cgctcgctgt ccgctagccc gctgcgatgt tgcgcgctgc cgcccgcttc     120
gggccccgcc tgggccgccg cctcttgtca gccgccgcca cccaggccgt gcctgccccc     180
aaccagcagc ccgaggtctt ctgcaaccag attttcataa acaatgaatg gcacgatgcc     240
gtcagcagga aaacattccc caccgtcaat ccgtccactg agaggtcat ctgtcaggta      300
gctgaagggg acaaggaaga tgtggacaag gcagtgaagg ccgcccgggc cgccttccag     360
ctgggctcac cttggcgccg catggacgca tcacacaggg gccggctgct gaaccgcctg     420
gccgatctga tcgagcggga ccggacctac ctggcggcct ggagaccct ggacaatggc      480
aagccctatg tcatctccta cctggtggat ttggacatgg tcctcaaatg tctccgggtat    540
tatgccggct gggctgataa gtaccacggg aaaaccatcc ccattgacgg agacttcttc     600
agctacacac gccatgaacc tgtggggtg tgcgggcaga tcattccgtg gaatttcccg      660
ctcctgatgc aagcatggaa gctgggccca gccttggcaa ctggaaacgt ggttgtgatg     720
aaggtagctg agcagacacc cctcaccgcc ctctatgtgg ccaacctgat caaggaggct     780
ggctttcccc ctggtgtggt caacattgtg cctggatttg ccccacggc tggggccgcc      840
attgcctccc atgaggatgt ggacaaagtg gcattcacag gctccactga gattggccgc     900
gtaatccagg ttgctgctgg gagcagcaac ctcaagagag tgaccttgga gctggggggg     960
```

-continued

```
aagagcccca acatcatcat gtcagatgcc gatatggatt gggccgtgga acaggcccac    1020
ttcgccctgt tcttcaacca gggccagtgc tgctgtgccg gctcccggac cttcgtgcag    1080
gaggacatct atgatgagtt tgtggagcgg agcgttgccc gggccaagtc tcgggtggtc    1140
gggaacccct tgatagcaa gaccgagcag gggccgcagg tggatgaaac tcagtttaag     1200
aagatcctcg gctacatcaa cacggggaag caagaggggg cgaagctgct gtgtggtggg    1260
ggcattgctg ctgaccgtgg ttacttcatc cagcccactg tgtttggaga tgtgcaggat    1320
ggcatgacca tcgccaagga ggagatcttc gggccagtga tgcagatcct gaagttcaag    1380
accatagagg aggttgttgg gagagccaac aattccacgt acgggctggc cgcagctgtc    1440
ttcacaaagg atttggacaa ggccaattac ctgtcccagg ccctccaggc gggcactgtg    1500
tgggtcaact gctatgatgt gtttggagcc cagtcaccct tggtggcta caagatgtcg     1560 gggagtggcc gggagttggg cgagtacggg ctgcaggcat acactgaagt gaaaactgtc    1620
acagtcaaag tgcctcagaa gaactcataa gaatcatgca agcttcctcc ctcagccatt    1680
gatggaaagt tcagcaagat cagcaacaaa accaagaaaa atgatccttg cgtgctgaat    1740
atctgaaaag agaaattttt cctacaaaat ctcttgggtc aagaaagttc tagaatttga    1800
attgataaac atggtgggtt ggctgagggt aagagtatat gaggaacctt ttaaacgaca    1860
acaatactgc tagctttcag gatgattttt aaaaaataga ttcaaatgtg ttatcctctc    1920
tctgaaacgc ttcctataac tcgagtttat aggggaagaa aaagctattg tttacaatta    1980
tatcaccatt aaggcaactg ctacaccctg ctttgtattc tgggctaaga ttcattaaaa    2040
actagctgct cttaacttac aaaaaaaaaa aaaaaa                              2076
```

<210> SEQ ID NO 24
<211> LENGTH: 1935
<212> TYPE: DNA
<213> ORGANISM: Artificial Sequence
<220> FEATURE:
<223> OTHER INFORMATION: Synthetic aldH2 gene NM_001204889.1 (Homo
      sapiens)

<400> SEQUENCE: 24

```
attggctgcc gcgcggggcg gggagcgggg tcggctcagt ggccctgaga ccctagctct     60
gctctcggtc cgctcgctgt ccgctagccc gctgcgatgt tgcgcgctgc cgcccgcttc    120
gggccccgcc tgggccgccg cctcttgtca gccgccgcca cccaggccgt gcctgccccc    180
aaccagcagc ccgaggtctt ctgcaaccag attttcataa acaatgaatg gcacgatgcc    240
gtcagcagga aaacattccc caccgtcaat ccgtccactg gagaggtcat ctgtcaggta    300
gctgaagggg acaaggcctt ggagaccctg gacaatggca gccctatgt catctcctac     360 ctggtggatt tggacatggt cctcaaatgt ctccggtatt atgccggctg ggctgataag    420
taccacggga aaaccatccc cattgacgga gacttcttca gctacacacg ccatgaacct    480
gtgggggtgt gcgggcagat cattccgtgg aatttcccgc tcctgatgca agcatggaag    540
ctgggcccag ccttggcaac tggaaacgtg gttgtgatga aggtagctga gcagacaccc    600
ctcaccgccc tctatgtggc caacctgatc aaggaggctg gctttccccc tggtgtggtc    660
aacattgtgc ctggatttgg ccccacggct ggggccgcca ttgcctccca tgaggatgtg    720
gacaaagtgg cattcacagg ctccactgag attggccgcg taatccaggt tgctgctggg    780
agcagcaacc tcaagagagt gaccttggag ctgggggga agagcccaa catcatcatg      840 tcagatgccg atatggattg gccgtggaa caggcccact tcgccctgtt cttcaaccag     900
```

```
ggccagtgct gctgtgccgg ctcccggacc ttcgtgcagg aggacatcta tgatgagttt    960
gtggagcgga gcgttgcccg ggccaagtct cgggtggtcg ggaacccctt tgatagcaag   1020
accgagcagg ggccgcaggt ggatgaaact cagtttaaga agatcctcgg ctacatcaac   1080
acggggaagc aagaggggc gaagctgctg tgtggtgggg gcattgctgc tgaccgtggt   1140
tacttcatcc agcccactgt gtttggagat gtgcaggatg gcatgaccat cgccaaggag   1200
gagatcttcg ggccagtgat gcagatcctg aagttcaaga ccatagagga ggttgttggg   1260
agagccaaca attccacgta cgggctggcc gcagctgtct tcacaaagga tttggacaag   1320
gccaattacc tgtcccaggc cctccaggcg ggcactgtgt gggtcaactg ctatgatgtg   1380
tttggagccc agtcacccct tggtggctac aagatgtcgg ggagtggccg ggagttgggc   1440
gagtacgggc tgcaggcata cactgaagtg aaaactgtca cagtcaaagt gcctcagaag   1500
aactcataag aatcatgcaa gcttcctccc tcagccattg atggaaagtt cagcaagatc   1560
agcaacaaaa ccaagaaaaa tgatccttgc gtgctgaata tctgaaaaga gaaatttttc   1620
ctacaaaatc tcttgggtca agaaagttct agaatttgaa ttgataaaca tggtgggttg   1680
gctgagggta agagtatatg aggaacccttt taaacgacaa caatactgct agctttcagg   1740 atgatttta aaaatagat tcaaatgtgt tatcctctct ctgaaacgct tcctataact   1800
cgagtttata ggggaagaaa aagctattgt ttacaattat atcaccatta aggcaactgc   1860
tacaccctgc tttgtattct gggctaagat tcattaaaaa ctagctgctc ttaacttaca   1920
aaaaaaaaaa aaaaa                                                     1935

<210> SEQ ID NO 25
<211> LENGTH: 1560
<212> TYPE: DNA
<213> ORGANISM: Artificial Sequence
<220> FEATURE:
<223> OTHER INFORMATION: Synthetic ald4 gene NM_001183794.1 (S.
      cerevisiae)

<400> SEQUENCE: 25
atgttcagta gatctacgct ctgcttaaag acgtctgcat cctccattgg gagacttcaa     60
ttgagatatt tctcacacct tcctatgaca gtgcctatca agctgcccaa tgggttggaa    120
tatgagcaac caacgggtt gttcatcaac aacaagtttg ttccttctaa acagaacaag    180
accttcgaag tcattaaccc ttccacggaa gaagaaatat gtcatattta tgaaggtaga    240
gaggacgatg tggaagaggc cgtgcaggcc gccgaccgtg ccttctctaa tgggtcttgg    300
aacggtatcg accctattga cagggtaag gctttgtaca ggttagccga attaattgaa    360
caggacaagg atgtcattgc ttccatcgag actttggata acggtaaagc tatctcttcc    420
tcgagaggag atgttgattt agtcatcaac tatttgaaat cttctgctgg ctttgctgat    480
aaaattgatg gtagaatgat tgatactggt agaacccatt tttcttacac taagagacag    540 cctttggtg tttgtgggca gattattcct tggaatttcc cactgttgat gtgggcctgg    600
aagattgccc ctgctttggt caccggtaac accgtcgtgt tgaagactgc cgaatccacc    660
ccattgtccg ctttgtatgt gtctaaatac atcccacagg cgggtattcc acctggtgtg    720
atcaacattg tatccgggtt tggtaagatt gtgggtgagg ccattacaaa ccatccaaaa    780 atcaaaagg ttgccttcac agggtccacg gctacgggta gacacatta ccagtccgca    840 gccgcaggct tgaaaaaagt gactttggag ctgggtggta atcaccaaa cattgtcttc    900 gcggacgccg agttgaaaaa agccgtgcaa aacattatcc ttggtatcta ctacaattct    960
```

```
ggtgaggtct gttgtgcggg ttcaagggtg tatgttgaag aatctattta cgacaaattc    1020
attgaagagt tcaaagccgc ttctgaatcc atcaaggtgg gcgacccatt cgatgaatct    1080
actttccaag gtgcacaaac ctctcaaatg caactaaaca aaatcttgaa atacgttgac    1140
attggtaaga atgaaggtgc tactttgatt accggtggtg aaagattagg tagcaagggt    1200
tacttcatta agccaactgt ctttggtgac gttaaggaag acatgagaat tgtcaaagag    1260
gaaatctttg gccctgttgt cactgtaacc aaattcaaat ctgccgacga agtcattaac    1320
atggcgaacg attctgaata cgggttggct gctggtattc acacctctaa tattaatacc    1380
gccttaaaag tggctgatag agttaatgcg ggtacggtct ggataaacac ttataacgat    1440
ttccaccacg cagttccttt cggtgggttc aatgcatctg gtttgggcag ggaaatgtct    1500
gttgatgctt tacaaaacta cttgcaagtt aaagcggtcc gtgccaaatt ggacgagtaa    1560
```

3-HYDROXYPROPIONIC ACID-PRODUCING RECOMBINANT MICROORGANISM AND METHOD OF PRODUCING 3-HYDROXYPROPIONIC ACID USING THE SAME

CROSS-REFERENCE TO RELATED APPLICATIONS

This application claims the benefit of Korean Patent Application No. 10-2012-0071367 filed on Jun. 29, 2012 in the Korean Intellectual Property Office, the entire disclosure of which is hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 36,494 Byte ASCII (Text) file named, "719069 ST25.TXT-Revised2" created May 6, 2015.

TECHNICAL FIELD

Provided is a method of producing 3-hydroxypropionic acid and recombinant microorganism used thereof. In particular, provided is a recombinant microorganism including a nucleic acid sequence encoding glycerol dehydratase derived from *Ilyobacter polytropus* and a nucleic acid sequence encoding dehydrogenase, which converts 3-hydroxypropionaldehyde into 3-hydroxypropionic acid, and a method of producing 3-hydroxypropionic acid comprising the step of culturing the same.

BACKGROUND ART

Recently, with the problems of petroleum-based industries such as global warming and serious fluctuations and increase in the cost of petroleum and the like, bio-based chemical and energy industries have received attention. Bio-diesel, a bio-fuel, is produced by the ester change reaction of triglyceride from vegetable oil or animal fat. Due to the mass-production of bio-diesel, the production of glycerol by-products rapidly increased, and the cost of the mass-produced glycerol is continuously decreasing. It is expected that in the future, with increased market demand for bio-diesel, the production amount of the glycerol by-products will rapidly increase and the cost of glycerol will be further lowered.

Glycerol may be used as fats and fatty oils, fiber, antistatic agents of leather, and raw material of emulsifiers for cleaning. In addition, it may also be used as a carbon source for microorganisms, and thus, various chemicals may be produced based on microorganisms using the same. Among them, 3-hydroxypropionic acid (3-HP) is a promising platform chemical raw material that can be used as a raw material of various chemicals, along with lactic acid and succinic acid, and it may be produced from microorganisms based on glycerol. 3-HP has two functional groups that perform important functions for the synthesis of optically active materials, which is an element causing 3-HP to be highly favored as an important precursor in the chemical industry. The main compounds synthesized using 3-HP as a precursor include acrylic acid (MW 72.06), malonic acid (MW 104.06), 1,3-propanediol (MW 76.06) and the like (See FIG. 1).

As shown in FIG. 1, biologically, 3-HP may be produced from glycerol through dehydration and oxidation processes catalyzed by two kinds of enzymes. Using the first enzyme, glycerol dehydratase, glycerol is dehydrated and converted into 3-hydroxypropionaldehyde (3-HPA), and the second enzyme 3-hydroxypropionaldehyde dehydrogenase (3-HPA dehydrogenase) oxidizes 3-HPA to produce 3-HP.

Glycerol dehydratase is classified into two kinds according to the method of action.

First, *Clostridium butyricum*-derived glycerol dehydratase is a vitamin $B_{12}$ non-dependent enzyme, and was reported to show the activity without aid of vitamin $B_{12}$, but it has extreme oxygen sensitivity (PNAS, 100: pp 5010-5015 (2003)). Although the production of 3-HP using the vitamin $B_{12}$ non-dependent glycerol dehydratase does not require vitamin $B_{12}$ and thus may lower the unit cost of production, when a recombinant microorganism is made to produce 3-HP, it has a difficulty with fermentation due to extremely high oxygen sensitivity.

Next, *Klebsiella pneumonia*-derived glycerol dehydratase is known as a vitamin $B_{12}$-dependent enzyme (U.S. Pat. No. 6,852,517). It is a vitamin $B_{12}$-dependent enzyme, and although vitamin $B_{12}$ should be added when used for the production of 3-HP, it exhibits high activity in common aerobic microorganism including *E. coli*, and thus, is relatively favorable for the production of 3-HP with high concentration compared to the vitamin non-dependent enzyme.

Meanwhile, 3-HPA, which is an intermediate in the production of 3-HP, may also be used as an intermediate for producing 1,3-propanediol (PDO). Namely, after glycerol is converted into 3-HPA, it may be converted into 1,3-propanediol by 1,3-PDO oxidoreductase, and in order to increase the production of 3-HP, it is required to inhibit the production of 1,3-PDO.

DISCLOSURE

Technical Problem

An embodiment provides a method of producing 3-hydroxypropionic acid that has excellent 3-hydroxypropionic acid productivity and low by-product production, and recombinant microorganism involved in the biosynthesis of 3-hydroxypropionic acid.

Technical Solution

One embodiment of the invention provides a method of producing 3-hydroxypropionic acid comprising the step of culturing recombinant microorganism comprising a nucleic acid sequence encoding *Ilyobacter polytropus*-derived glycerol dehydratase and a nucleic acid sequence encoding dehydrogenase, which converts 3-hydroxypropionaldehyde into 3-hydroxypropionic acid.

Another embodiment of the invention provides an expression cassette operably comprising a transcription promoter, a nucleic acid sequence encoding glycerol dehydratase, a nucleic acid sequence encoding a glycerol dehydratase reactivator, and a transcription terminator.

Still another embodiment of the invention provides recombinant microorganism comprising the expression cassette and involved in the biosynthesis of 3-hydroxypropioic acid.

Advantageous Effects

According to the method of producing 3-hydroxypropionic acid and recombinant microorganism used therefor according to the present invention, the production of 3-hydroxypropion remarkably increases compared to the previously reported recombinant microorganism comprising a gene expressing *klebsiella pneumonia*-derived Vitamin $B_{12}$-dependent glycerol dehydratase, and the production amount of 1,3-propanediol (1,3-PDO) that is generated as a by-product when producing 3-hydroxypropionic acid remarkably decreases.

Accordingly, a large quantity of 3-hydroxypropionic acid may be economically obtained using the recombinant microorganism of the present invention.

MODE FOR INVENTION

Figure 1:
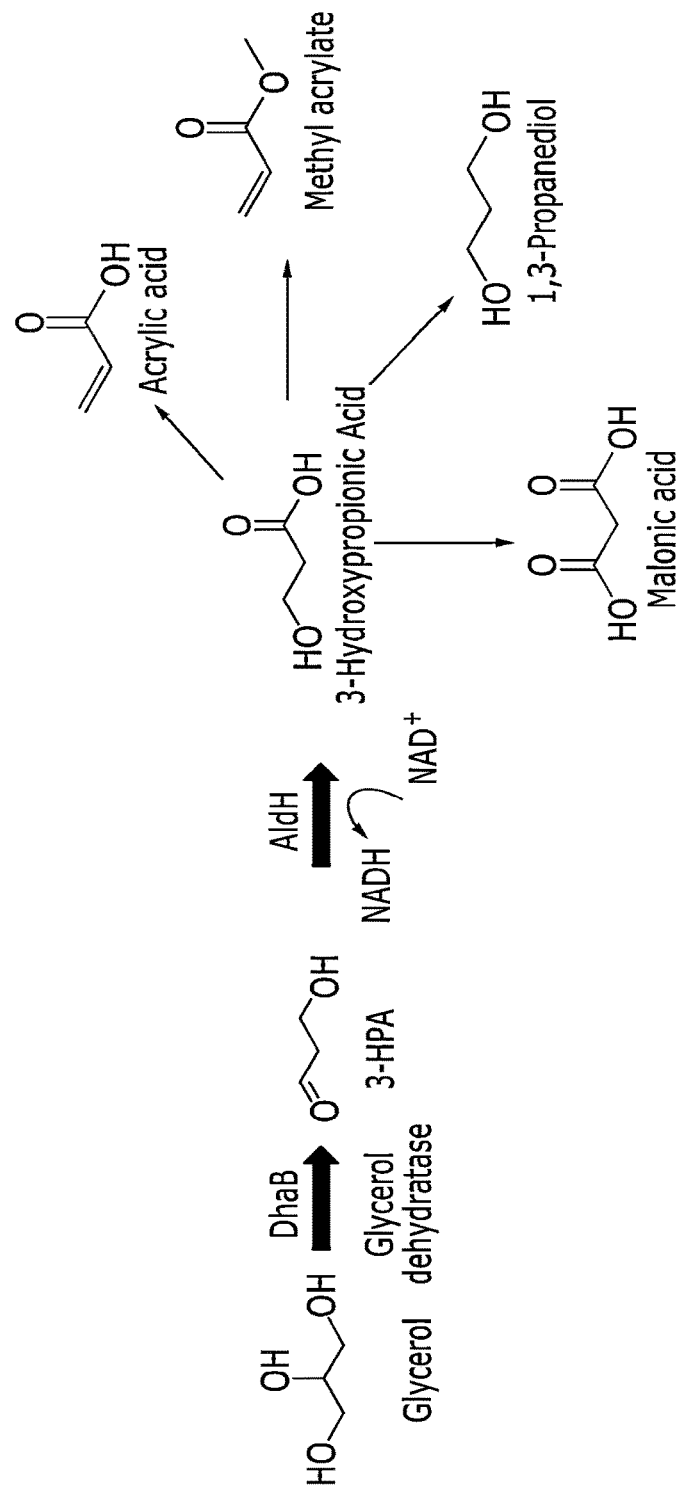
FIG. 1 is a schematic drawing showing the pathway of producing 3-hydroxypropionic acid from glycerol and the main compounds synthesized using the same as a precursor.

Before specifically describing the invention, the meanings of the terms used herein will be described.

As used herein, the term 'polypeptide' is interpreted as comprising an amino acid sequence showing substantial identity to corresponding amino acid sequence. The substantial identity means that an amino acid sequence shows at least 80%, preferably at least 90% homology, when the amino acid sequence and any other sequence are aligned so that they are corresponded to the maximum, and the aligned sequences are analyzed using algorithm commonly used in the art.

For example, the polypeptide includes polypeptide that have an amino acid sequence having about 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more identity to specific amino acid sequence, and is involved in the biosynthesis of 3-hydroxypropionic acid. In general, as the identity percent is higher, it is more preferable.

And, the polypeptide having identity includes polypeptide that comprises an amino acid sequence having the deletion, substitution, insertion, and/or addition of an amino acid residue in the polypeptide of specific amino acid sequence, and is involved in the biosynthesis of 3-hydroxypropionic acid. In general, as the number of deletion, substitution, insertion, and/or addition is smaller, it is more preferable.

As used herein, the term 'polynucleotide' means to comprehensively include DNA (gDNA and cDNA) and RNA molecules, and nucleotide, which is the basic unit of a nucleic acid molecule, also includes sugar or base-modified analogues, as well as natural nucleotide.

It is interpreted that the polynucleotide of the present invention is not limited to a nucleic acid molecule encoding the above described specific amino acid sequence (polypeptide), and includes nucleic acid molecules encoding amino acid sequences showing substantial identity to the amino acid sequence or polypeptide having a function corresponding thereto. The substantial identity means that an amino acid sequence shows at least 80%, preferably at least 90% identity, when the amino acid sequence of the present invention and any other sequence are aligned so that they are corresponded to the maximum, and the aligned sequences are analyzed using algorithm commonly used in the art.

The polypeptide having a corresponding function includes, for example, polypeptides with an amino acid sequence having the deletion, substitution, insertion, and/or addition of at least one amino acid residue. Such polypeptides include polypeptides that consist of an amino acid sequence having the deletion, substitution, insertion, and/or addition of at least one amino acid residue, and are involved in the synthesis of 3-hydroxypropioni acid.

The identity between amino acid sequences or nucleotide sequences may be measured using the BLAST algorithm by Karlin and Altschul, according to BLASTN and BLASTX programs based on a BLAST algorithm. When a nucleotide sequence is sequenced using BLASTN, the parameters of, for example, score=100 and word length=12 can be used. If an amino acid sequence is sequenced using BLASTX, the parameters of, for example, score=50 and word length=3 can be used. In case BLAST and Gapped BLAST programs are used, default parameters are applied for each program.

The present invention provides a method of producing 3-hydroxypropionic acid comprising the step of culturing recombinant microorganism comprising a nucleic acid sequence encoding *Ilyobacter polytropus*-derived glycerol dehydratase and a nucleic acid sequence encoding dehydrogenase, which converts 3-hydroxypropionaldehyde into 3-hydroxypropionic acid, and microorganism used therefor. Hereinafter, the present invention will be explained in detail with reference to the attached drawings.

The *Ilyobacter polytropus*-derived glycerol dehydratase' of the present invention refers to a polypeptide having the enzymatic activity of converting glycerol into 3-hydroxypropionaldehyde (3HPA)

The glycerol dehydratase of the present invention may allow a microorganism to use glycerol as a substrate, and it has superior activity of converting glycerol into 3-HPA, compared to the known vitamin $B_{12}$-dependent *Klebsiella pneumonia*-derived glycerol dehydratase. And, it has appropriate balance with dehydrogenase for converting 3HPA into 3-HP, and thus, may minimize the production pathway of 1,3-PDO to decrease the production amount of 1,3-PDO.

The *Ilyobacter polytropus*-derived glycerol dehydratase consists of 3 structural subunits of SEQ ID NO. 2, SEQ ID NO. 4, and SEQ ID NO. 6, which respectively correspond to DhaB1, DhaB2 and DhaB3 making up the α, β and γ subunits of a glycerol dehydratase enzyme.

More specifically, the amino acid sequence of SEQ ID NO. 2 corresponds to *Ilyobacter polytropus*-derived DhaB1, the amino acid sequence of SEQ ID NO. 4 corresponds to *Ilyobacter polytropus*-derived DhaB2, and the amino acid sequence of SEQ ID NO. 6 corresponds to *Ilyobacter polytropus*-derived DhaB3.

Meanwhile, the nucleic acid sequence of SEQ ID NO. 1 corresponds to *Ilyobacter polytropus*-derived dhaB1, the nucleic acid sequence of SEQ ID NO. 3 corresponds to *Ilyobacter polytropus*-derived dhaB2, and the nucleic acid sequence of SEQ ID NO. 5 corresponds to *Ilyobacter polytropus*-derived dhaB3.

Thus, the nucleic acid sequence encoding glycerol dehydratase that can be used in the present invention may be a nucleic acid sequence encoding a polypeptide comprising the amino acid sequences of SEQ ID NO. 2, SEQ ID NO. 4, and SEQ ID NO. 6. Preferably, the nucleic acid sequence encoding glycerol dehydratase may be a nucleic acid sequence comprising all the α, β and γ subunits of a glycerol dehydratase enzyme, DhaB1, DhaB2 and DhaB3.

The nucleic acid sequence encoding glycerol dehydratase may comprise nucleic acid sequences of SEQ ID NO. 1, SEQ ID NO. 3, and SEQ ID NO. 5. Preferably, the nucleic acid sequence encoding glycerol dehydratase may comprise nucleic acid sequences comprising all the α, β and γ subunits of a glycerol dehydratase enzyme, namely, SEQ ID NO. 1, SEQ ID NO. 3 and SEQ ID NO. 5.

The 'dehydrogenase which converts 3-hydroxypropionaldehyde into 3-hydroxypropionic acid' of the present invention is named as 3-hydroxypropionaldehyde dehydrogenase (3-HP dehydrogenase), which is an enzyme capable of converting 3-HPA into 3-HP through a dehydrogenation reaction, and uses NAD+/NADH or NADP+/NADPH as a coenzyme.

The nucleic acid sequence encoding dehydrogenase which converts 3-hydroxypropionaldehyde into 3-hydroxypropionic acid may be selected from *Homo Sapiens*-derived aldH2 gene (NM _000690.3 (SEQ ID NO: 23), NM _ 001204889.1 (SEQ ID NO: 24)), *S. cerevisiae*-derived ald4 gene (NM _001183794.1 (SEQ ID NO: 25)), *E. coli*-derived aldA, aldB, aldH genes (SEQ ID NO. 11), and the like, but is not limited thereto. The nucleic acid sequence encoding dehydrogenase may be a nucleic acid sequence encoding polypeptide comprising the amino acid sequence as described SEQ ID NO. 12, which corresponds to *E. coli* K-12 derived AldH, and preferably, may be a nucleic acid sequence of SEQ ID NO. 11.

The glycerol dehydratase is irreversibly inactivated by glycerol or by the interaction with 1,3-propanediol while it performs a catalytic function. Thus, the recombinant microorganism for producing 3-HP of the present invention may further comprise a nucleic acid sequence encoding a glycerol dehydratase reactivator for activating dehydratase. As the glycerol dehydratase reactivator, those commonly known in the art may be used, and it is known in WO 98/21341 (U.S. Pat. No. 6,013,494), document [R. Daniel et Eur. J. Biochem., 268 (2001), pp. 2369-2378], document [Toraya and Mori, J. Biol. Chem. 274:3372 (1999)] and document [Tobimatsu et al., J. Bacteriol. 181:4110 (1999)]. The nucleic acid sequence encoding a dehydratase reactivator may be selected from *Citrobacter freundii*-derived gene dhaFG (ABI36568.1), *Klebsiella pneumonia*-derived gdrAB (EF077655.1), *Klebsiella oxytoca* ddrAB (AAC15871), *Ilyobacter polytropus*-derived GdrA (SEQ ID NO. 7) and GdrB (SEQ ID NO. 9), and the like.

Preferably, the nucleic acid sequence encoding a glycerol dehydratase reactivator may comprise a nucleic acid sequence encoding polypeptide comprising the amino acid sequences of SEQ ID NO. 8 and SEQ ID NO. 10, and preferably, it may comprise a nucleic acid sequence of SEQ ID NO. 7 and a nucleic acid sequence of SEQ ID NO. 9.

Another embodiment of the invention provides an expression cassette operably comprising a transcription promoter, a nucleic acid sequence encoding glycerol dehydratase, a nucleic acid sequence encoding a glycerol dehydratase reactivator, and a transcription terminator.

The "expression cassette" of the present invention refers to a nucleic acid fragment comprising a nucleic acid sequence encoding gene and a regulatory sequence existing before and after the nucleic acid sequence, and it typically is in a vector. The expression cassette generally comprises a promoter sequence, a sequence-encoding gene, and a transcription terminator sequence.

"The transcription promoter" of the present invention refers to a DNA sequence controlling the expression of coding sequence, including enhancers. The promoter may be a gene's natural promoter or derived from another promoter. As used herein, the description that a promoter is "operably linked" means that the promoter is linked to a coding sequence so that the coding sequence may be expressed. The "transcription terminator sequence" of the present invention means a DNA sequence existing downstream of a sequence encoding gene(s).

The promoter that can be used in the present invention may include CYC1, HIS3, GAL1, GAL10, ADH1, PGK, PH05, GAPDH, ADC1, TRP1, URA3, LEU2, ENO, and lac, ara, tet, trp, T7, tac, trc, amy, apr, npr, and the like.

Still another embodiment of the invention provides a microorganism comprising the expression cassette and involved in the biosynthesis of 3-hydroxypropionic acid.

In the microorganism according to the present invention, the nucleic acid sequence encoding a glycerol dehydratase reactivator and the nucleic acid sequence encoding glycerol dehydratase may be derived from identical microorganism species, and it is most preferable in terms of the synthesis efficiency of 3-hydroxypropionic acid that both are derived from *Ilyobacter polytropus*.

Thus, the recombinant microorganism according to the present invention may be preferably indicated as comprising nucleotides encoding polypeptides of SEQ ID NO. 2 (DhaB1), SEQ ID NO. 4 (DhaB1) and SEQ ID NO. 6 (DhaB1), SEQ ID NO. 8 (GdrA), SEQ ID NO. 10 (GdrB) and SEQ ID NO. 12 (AldH), and more preferably, it may be indicated as comprising nucleotides of SEQ ID NO. 1 (dhaB1), SEQ ID NO. 3 (dhaB1), SEQ ID NO. 5 (dhaB1), SEQ ID NO. 7 (gdrA), SEQ ID NO. 9 (gdrB) and SEQ ID NO. 11 (aldh).

The microorganism that can be used to obtain the recombinant microorganism of the present invention is not specifically limited as long as it may express the corresponding gene, and it may be selected from the group consisting of bacteria, yeast and mold. Preferably, it is selected from the genus group consisting of *Escherichia, Citrobacter, Enterobacter, Clostridium, Klebsiella, Lactobacillus, Aspergillus, Saccharomyces, Schizosaccharomyces, Zygosaccharomyces, Pichia, Kluyveromyces, Candida, Hansenula, Salmonella, Bacillus, Streptomyces* and *Pseudomonas*. More preferably, it is *E. coli*.

In the present invention, any known method can be used to construct the expression cassette and recombinant microorganism that can be used in the dehydration reaction of glycerol. The constructed expression cassette is introduced into a suitable host cell using any known method. Specifically, transformation by heat shock or electroporation and the like, transfection using a recombinant phage, and the like may be used. The introduced expression cassette may be maintained extrachromosomally, or it may be integrated into chromosome by homologous recombination or random recombination using a vector using known technology.

The method of producing 3-hydroxypropionic acid of the present invention or the culture of recombinant microorganism used in the biosynthesis of 3-hydroxypropionic acid may be conducted in the presence of at least one carbon source selected from the group consisting of monosaccharides, oligosaccharides, polysaccharides, or glycerol. Among them, it is preferable in terms of the production efficiency of 3-HP and economical feasibility that glycerol is included as carbon source, and glucose is further included to facilitate cell growth. In the case of a microorganism that cannot naturally convert glucose into glycerol, foreign genes required for the conversion may be introduced by any known method to allow the production of 3-HP from glucose. To the medium used for the culture, vitamin $B_{12}$ may be added.

The culture conditions may be appropriately controlled according to the used host cell, and for example, the culture of *E. coli* may be conducted under aerobic conditions, pH 6~7.6, at a temperature of 30° C. or more, preferably at a temperature of 33~37° C., for 1~4 days. In this case, cell growth may be active and 3-hydroxypropionic acid may be efficiently produced. As to the culture temperature, since enzymes and microorganisms stable at high temperature are used, cooling is not required to maintain the culture temperature, thus reducing additional facility for cooling and the like and the resulting cost. In the process of producing 3-HP using a microorganism, the culture temperature increases due to culture heat generated by microorganism culture, and if enzymes or microorganisms having high stability even under increased culture temperature condition are used, 3-HP may be continuously produced with high efficiency under stabilized condition.

The present invention may be conducted batchwise, pad-batchwise, or continuously, and any known fermentation method may be appropriate. And, the cell may be fixed on a substrate and fermented.

It was confirmed that since the *Ilyobacter polytropus*-derived glycerol dehydratase according to the present invention exhibits superior productivity of 3-hydroxypropionic acid, and decreases the production of 1,3-propanediol, compared to the previously reported *Klebsiella pneumonia*-derived glycerol dehydratase, it may be effectively used in the production of 3-hydroxypropionic acid instead of the existing *Klebsiella pneumonia*-derived glycerol dehydratase.

The present invention will be explained in detail with reference to the following examples. However, these examples are only to illustrate the invention, and it is not to be understood that the scope of the invention is limited thereto.

EXAMPLE 1

Construction of Recombinant Microorganism Comprising Genes Encoding *Ilyobacter polytropus*-Derived Glycerol Dehydratase <Step 1> Construction of a Recombinant Vector Comprising Genes Expressing *Ilyobacter polytropus*-Derived Glycerol Dehydratase Genome DNA was extracted from *Ilyobacter polytropus* DSM 2926, and dhaB123-gdrA and gdrB genes were PCR amplified from the genome DNA respectively using the following primers and inserted respectively at the locations of NcoI-EcoRI and EcoRI-SacI of a pET-Duet (Novagen) vector to construct an ET-iBAB vector.

1) Primers Used for dhaB1, dhaB2 and dhaB3 Gene Amplification

```
Forward direction primer
(SEQ ID NO. 13: TCATGAAATCAAAAAGATTTGAAGT
ATTGAAG (BspHI))

Reverse direction primer
(SEQ ID NO. 14: GGATCCCTAATCTTTTCTAAGTTGA
CCTCTTTGTTC (BamHI))

2) Primers used for gdrA and gdrB gene
amplification
Forward direction primer
(SEQ ID NO. 15: GGATCCAAAGGTTCGGGGATAGTTA
TGAAG (BamHI))

Reverse direction primer
(SEQ ID NO. 16: GAGCTCTTATCTAAGTGGCAGACCC
TTTACAAG (SacI))
```

After PCR was completed, dhaB1, dhaB2 and dhaB3 were cleaved with BspHI and BamHI, and gdrA and gdrB were cleaved with BamHI and SacI.

PCR conditions are as follows: Use of Phusion high fidelity DNA polymerase (Thermo scientific), Cycle I (98° C., 30 sec), Cycle II (30 cycles/98° C., 10 sec/55° C., 1 min, 72° C., 2 min), Cycle III (72° C., 5 min).

Both amplified DNA fragments were inserted respectively at the locations of NcoI-EcoRI and EcoRI-SacI of a pET-Duet (Novagen) vector to construct ET-iBAB.

<Step 2> Construction of a Recombinant Vector Comprising Gene Encoding Aldehyde Dehydrogenase Genome DNA was extracted from *E. coli* K-12, and the aldH gene was amplified using the following primer, and cleaved with NdeI and Bgl II.

```
Forward direction primer
(SEQ ID NO. 17: TTTCATATGAATTTTCATCATCTGG
CTTAC (NdeI))

Reverse direction primer
(SEQ ID NO. 18: TTTAGATCTTTCGGTCATTTCAGGC
CTCCA (BglII))
```

PCR conditions were as follows: Use of LA taq polymerase (Takara, Japan), Cycle I (97° C., 5 min), Cycle II (31 cycles/97° C., 1 min/55° C., 1 min, 72° C., 3 min), Cycle III (72° C., 10 min). The amplified DNA was introduced into a pETDuet vector (Novagen) cleaved with the same enzyme to construct an ET-H vector.

Figure 2:
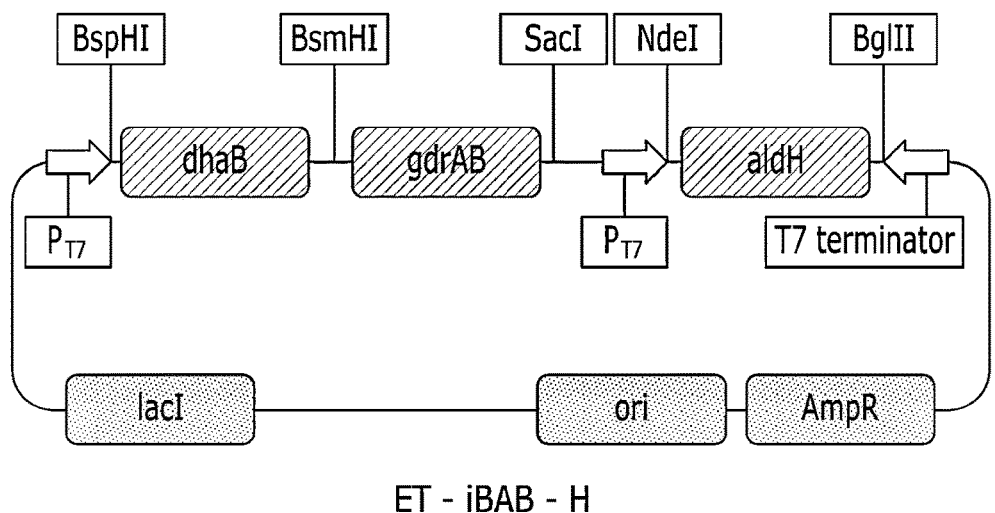
FIG. 2 is a schematic cleavage map of the recombinant vector (ET-iBAB-H) of Example 1.

<Step 3> Construction of a Recombinant Vector Comprising Genes for the Production of 3-HP The ET-H vector of the <Step 2> was treated with restriction enzymes SalI-HF and Avr II to obtain an aldH containing DNA fragment, which was introduced into the ET-iBAB vector of the <Step 1> treated with the same enzyme to construct an ET-iBAB-H vector (See FIG. 2).

FIG. 2 schematically shows the cleavage map of the recombination vector (ET-iBAB-H) of Example 1. 1) dhaB1, dhaB2 and dhaB3 genes are genes encoding *Ilyobacter polytropus*-derived glycerol dehydratase, 2) gdrA, gdrB are genes encoding *Ilyobacter polytropus*-derived glycerol dehydratase reactivator, and 3) aldH is gene encoding *E. coli* K-12-derived aldehyde dehydrogenase.

<Step 4> Construction of *E. coli* Transformed with a Recombination Vector

*E. coli* was transformed with the recombination vector ET-iBAB-H constructed in the <Step 3> to construct a recombinant strain.

COMPARATIVE EXAMPLE 1

Construction of Recombinant Microorganism Comprising Genes Encoding *Klebsiella pneumonia*-Derived Glycerol Dehydratase The genome DNA of *Klebsiella pneumonia* DSM 2026 was extracted, and dhaB123-gdrA and gdrB genes were PCR amplified using the following primers and inserted respectively into the locations of NcoI-EcoRI and EcoRI-SalI of a Pet-Duet (Novagen) vector to construct an ET-BAB vector.

1) Primers Used for dhaB123-gdrA Gene Amplification

```
Forward direction primer
(SEQ ID NO. 19: ATATCATGAAAAGATCAAAACGATT
T (BspHI))

Reverse direction primer
(SEQ ID NO. 20: AAAGAATTCCGCGAGCGCCCGTTTA
ATTC (EcoRI))

2) Primer used for gdrB gene amplification
Forward direction primer
(SEQ ID NO. 21: TTTGAATTCTAACGAGGGGACCGTC
ATGTC (EcoRI))
```

```
Reverse direction primer
(SEQ ID NO. 22: ATAGTCGACTCAGTTTCTCTCACTT
AACGG (SalI))
```

The PCR was conducted as a process of Cycle I (95° C., 5 minutes), Cycle II (30 cycles/95° C., 30 seconds/55° C., 30 seconds/72° C., 5 minutes (dhaB123-gdrA) or 30 seconds (gdrB)), and Cycle III (72° C., 5 minutes).

Genome DNA was extracted from *E. coli* K-12 to obtain aldH gene, the aldH gene was amplified using the following primer and cleaved with NdeI and BglII.

```
Forward direction primer
(SEQ ID NO. 17: TTTCATATGAATTTTCATCATCTGG
CTTAC (NdeI))

Reverse direction primer
(SEQ ID NO. 18: TTTAGATCTTTCGGTCATTTCAGGC
CTCCA (BglII))
```

PCR conditions were as follows: Use of LA taq polymerase (Takara, Japan), Cycle I (97° C., 5 min), Cycle II (31 cycles/97° C., 1 min/55° C., 1 min, 72° C., 3 min), Cycle III (72° C., 10 min).

Figure 3:
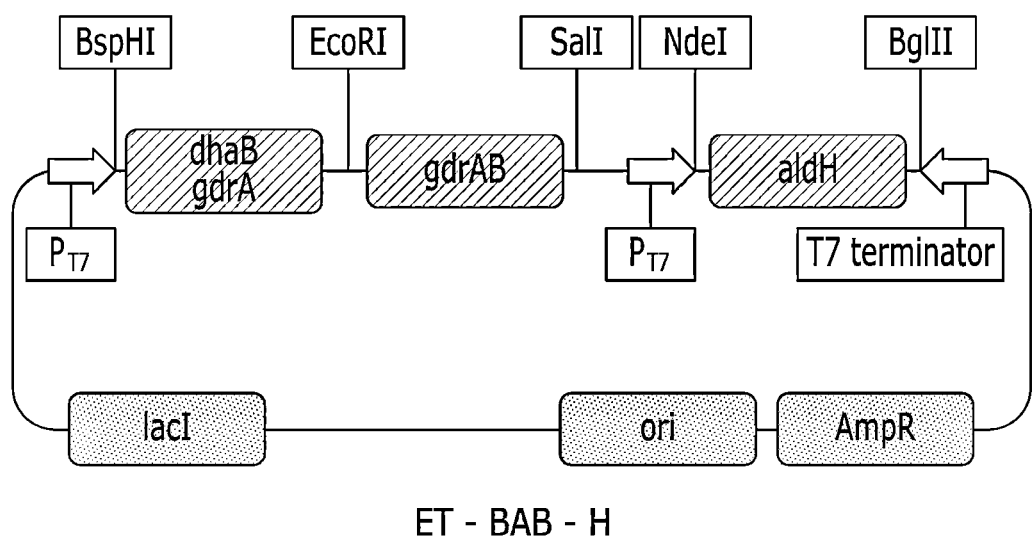
FIG. 3 is a schematic cleavage map of the recombinant vector (ET-BAB-H) of Comparative Example 1.
Figure 4:
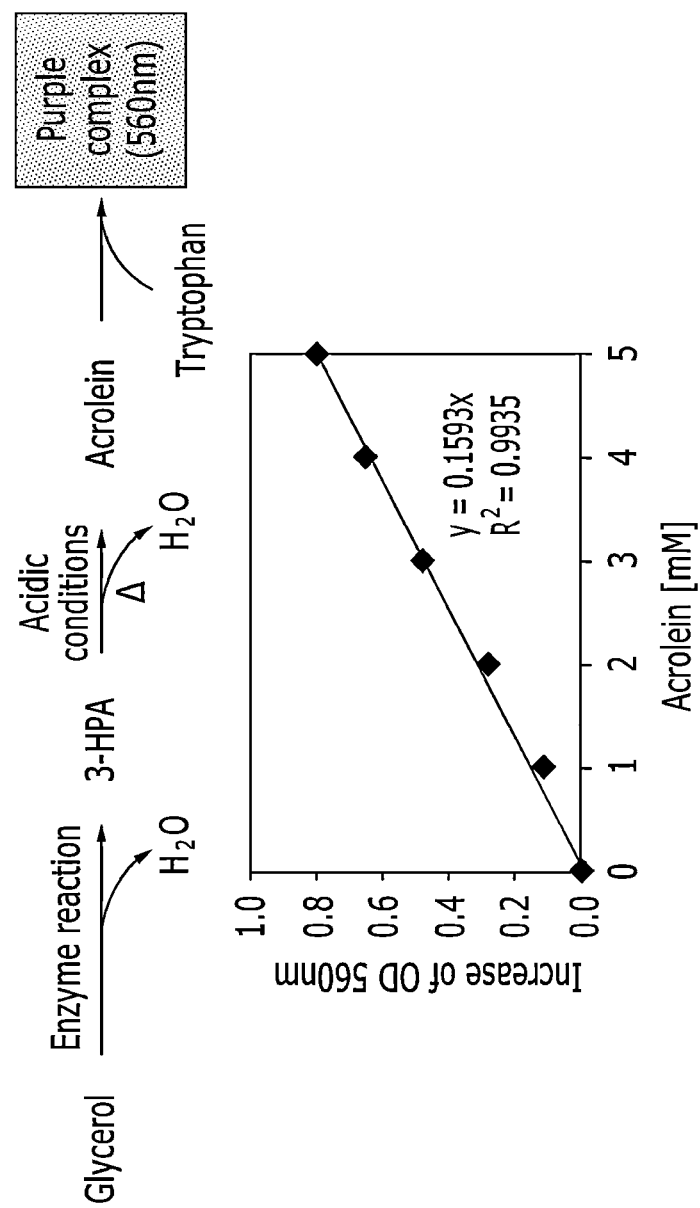
FIG. 4 schematically shows a method of measuring the concentration of 3-hydroxypropionaldehyde (3-HPA) using acrolein and tryptophan.

The amplified DNA was introduced into a pET-BAB cleaved with the same enzyme to construct an ET-BAB-H vector. *E. coli* was transformed with the constructed recombination vector ET-BAB-H to construct a recombinant strain (See FIG. 3).

FIG. 3 schematically shows the cleavage map of the recombination vector of Comparative Example 1 (ET-BAB-H). 1) dhaB1, dhaB2 and dhaB3 genes are *Klebsiella pneumonia*-derived glycerol dehydratase genes, 2) gdrA, gdrB are *Klebsiella pneumonia*-derived glycerol dehydratase reactivator genes, and 3) aldH is a gene encoding *E. coli* K-12-derived aldehyde dehydrogenase.

EXPERIMENTAL EXAMPLE 1

Synthesis of 3-Hydroxypropionic Acid (3-HP)

To culture the recombinant *E. coli* constructed in Example 1 and Comparative Example 1, 50 ml of LB medium was put in each 250 ml flask, and pre-culture was conducted in a 37° C. rotating culture apparatus for 12 hours. Thereafter, 50 ml of M9 medium was put in the 250 ml flask, and cultured in a 35° C. culture apparatus to induce the expression with 0.03 mM isopropyl β-D-thiogalactopyranoside (IPTG) at the optical density (OD) of 0.8. At 24 and 48 hours, a part of the culture liquid was extracted to measure the optical density (OD) and pH, and the production of 3-HP was confirmed by high performance liquid chromatography (HPLC).

For 3-HP analysis, an Aminex HPX-87H (300 mm*7.8 mm) column was used, and a solution containing 9% acetonitrile in a 0.5 mM sulfuric acid solution was used as a mobile phase and flowed at a flow rate of 0.4 ml/min. The temperature of the column was 35° C., and RI and UV/VIS (210 nm) dual mode was used as a detector. 3-HP was detected at 17.5 minute during the total analysis time of 35 minutes, and the production of 3-HP was also confirmed by Liquid chromatography/mass spectrometry (LC/MS).

Figure 5:
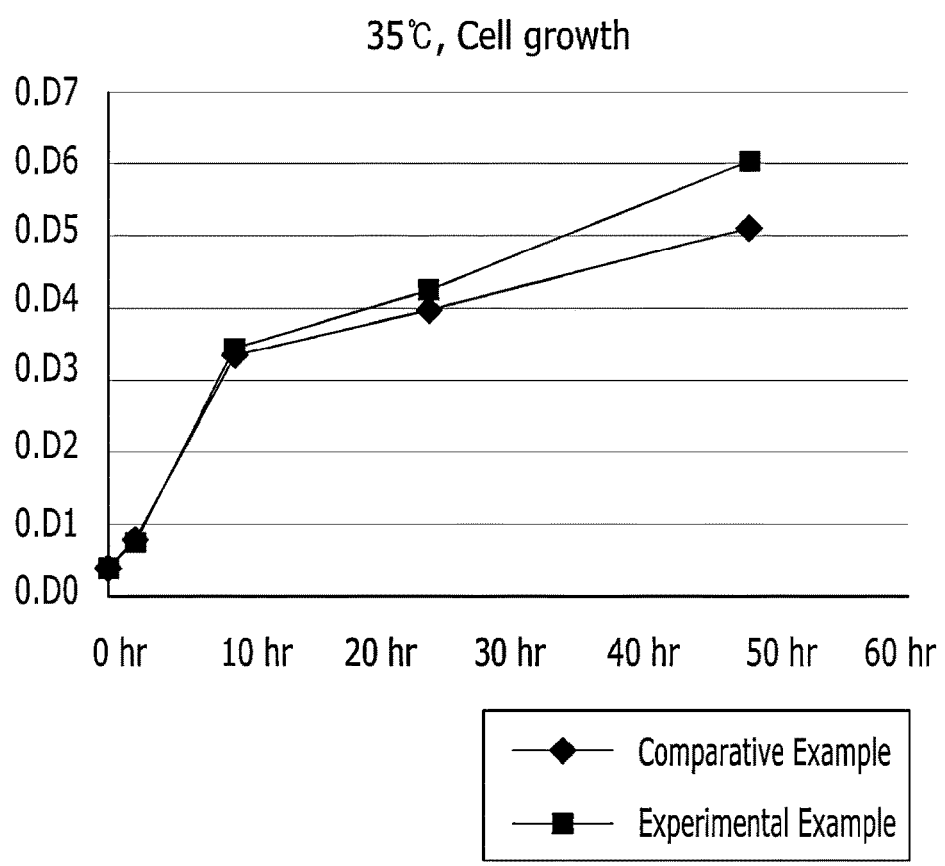
FIG. 5 shows the change in the concentration (OD) of cell culture fluid over time, in the production experiment of 3-HP using the recombinant *E. coli* constructed in Example 1 and Comparative Example 1, under culture condition of 35° C. according to Experimental Example 1.
Figure 6:
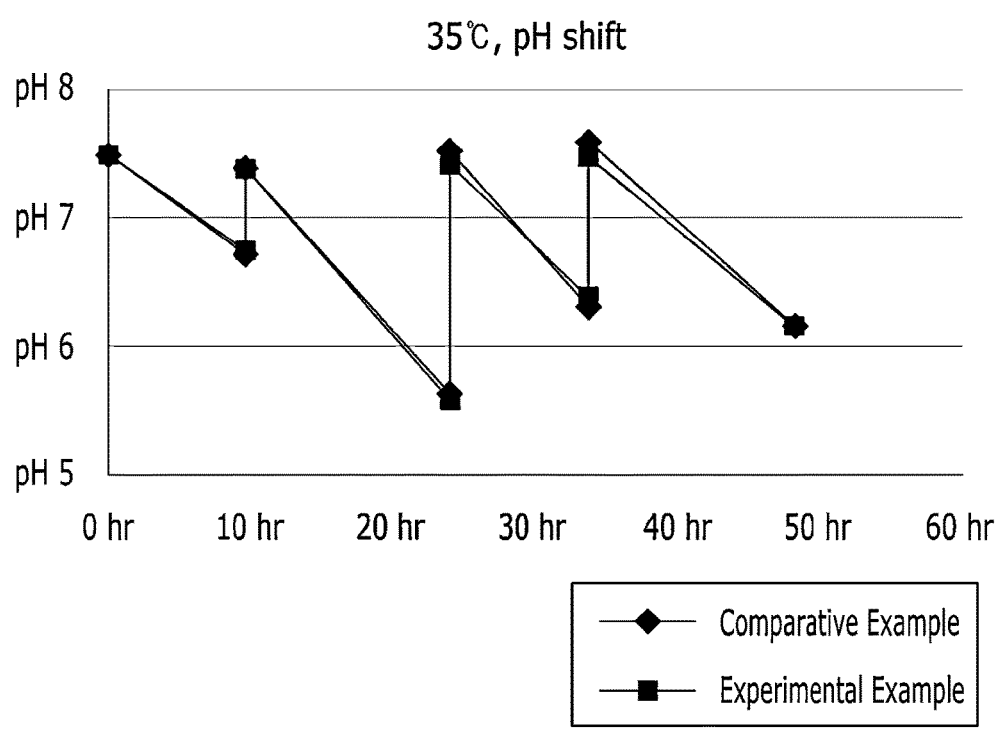
FIG. 6 shows the change in pH of cell culture fluid over time, in the production experiment of 3-HP using the recombinant *E. coli* constructed in Example 1 and Comparative Example 1, under culture condition of 35° C. according to Experimental Example 1.

As shown in FIG. 5 and FIG. 6, although OD values were similar up to 10 hours in both strains, the strain of Example 1 showed a little higher value than the strain of Comparative Example 1 after 10 hours, and the pH of the culture liquid showed a similar aspect.

Figure 7:
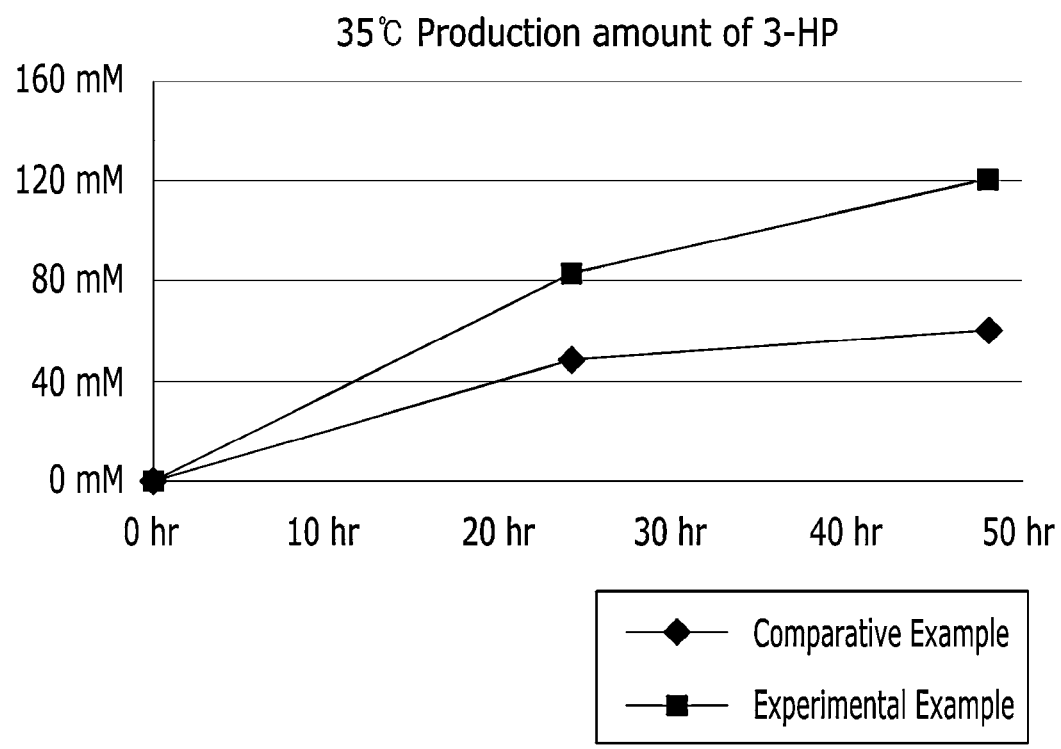
FIG. 7 shows the production amount of 3-HP over time, in the production experiment of 3-HP using the recombinant *E. coli* constructed in Example 1 and Comparative Example 1, under culture condition of 35° C. according to Experimental Example 1.

Meanwhile, as to the production amount of 3-HP, the strain of Comparative Example 1 showed 48.9 mM at 24 hours and 61.1 mM at 48 hours, while the strain of Example 1 according to the present invention showed high 3-HP production amount of 83.3 mM at 24 hours, and 121 Mm at 48 hours (FIG. 7).

Figure 8:
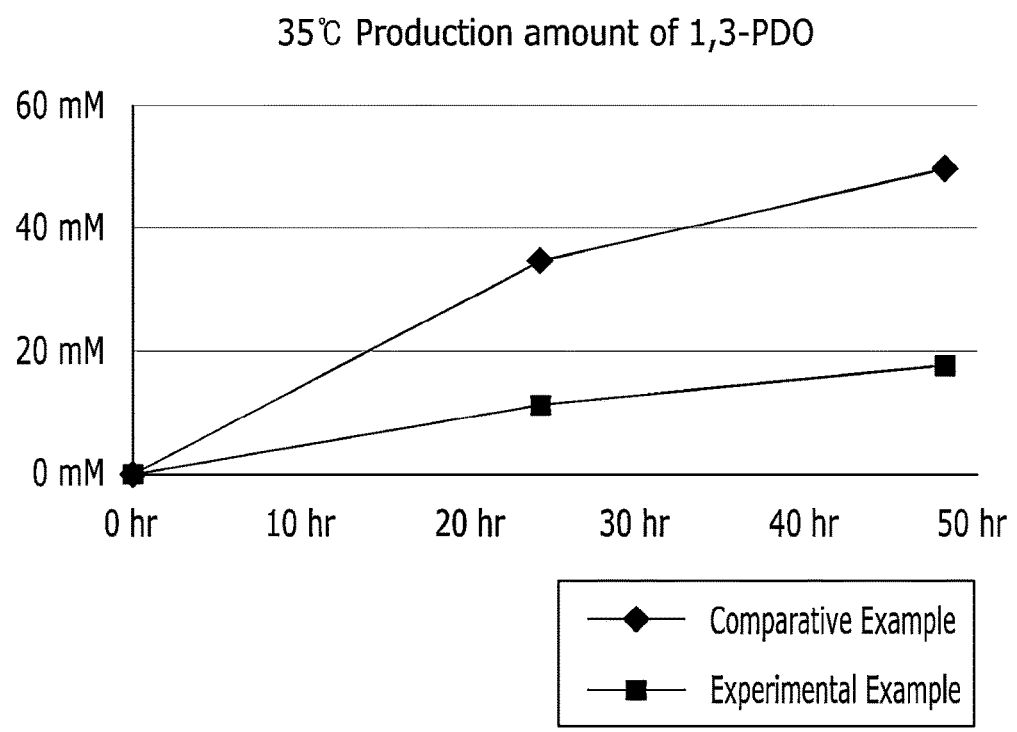
FIG. 8 shows the production amount of 1,3-PDO over time, in the production experiment of 3-HP using the recombinant *E. coli* constructed in Example 1 and Comparative Example 1, under culture condition of 35° C. according to Experimental Example 1.

And, as to the production amount of by-product 1,3-PDO, the strain of Comparative Example 1 showed 35.0 Mm at 24 hours and 50.0 mM at 48 hours, while the strain of Example 1 according to the present invention showed remarkably decreased by-product generation of 11.6 mM at 24 hours and 18.0 mM at 48 hours. (See FIG. 8)

Figure 9:
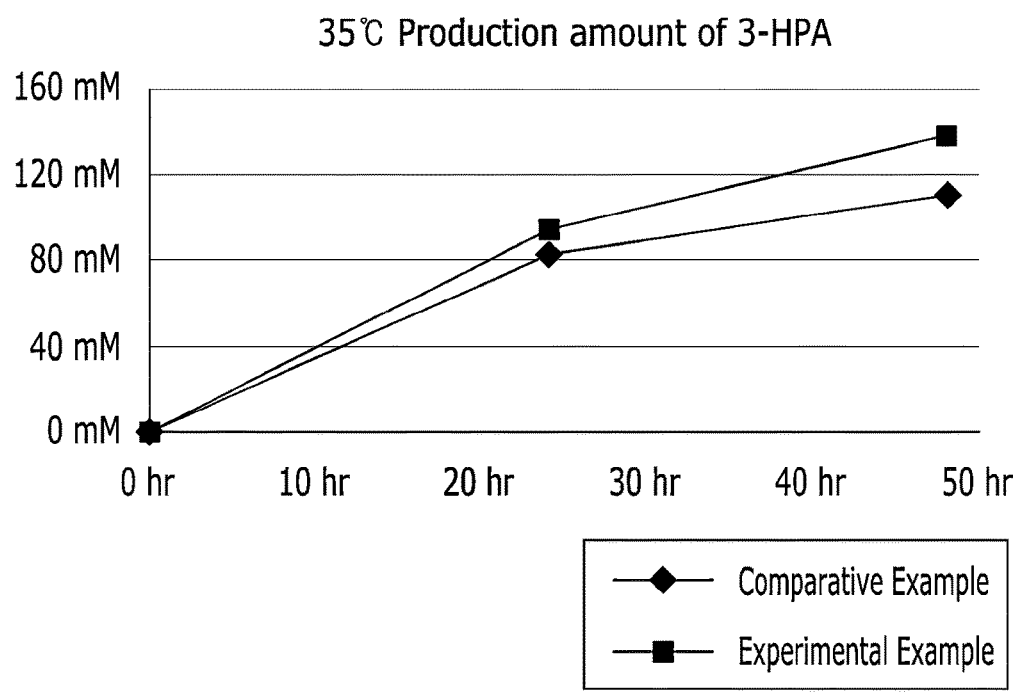
FIG. 9 shows the production amount of 3-HPA over time, in the production experiment of 3-HP using the recombinant *E. coli* constructed in Example 1 and Comparative Example 1, under culture condition of 35° C. according to Experimental Example 1.

The total activity of glycerol dehydratase may be indirectly confirmed by adding the production of 3-HP and the production of 1,3-PDO, and calculating the amount of 3-HPA (FIG. 9). Comparative Example 1 was measured as 83.8 mM at 24 hours and 111.0 mM at 48 hours, while the strain of Example 1 according to the present invention produced 94.9 mM of 3-HPA at 24 hours, and 139.0 mM of 3-HPA at 48 hours.

Thus, it was confirmed that in case *Ilyobacter polytropus*-derived glycerol dehydratase was used according to the present invention, the production amount of 3-HPA increased 25% and thus the production amount of 3-HP increased 96%, compared to the case of using the existing *klebsiella pneumonia*-derived glycerol dehydratase. Furthermore, the production amount of by-product 1,3-PDO decreased 64%, and thus, it can be seen that according to the present invention, the production of 3-HP increases, and the generation of 1,3-PDO decreases, thereby maximizing the production of 3-HP.

EXPERIMENTAL EXAMPLE 2

Synthesis of 3-Hydroxypropionic Acid (3-HP)

To culture the recombinant *E. coli* constructed in Example 1 and Comparative Example 1, 50 ml of LB medium was put in each 250 ml flask, and pre-culture was conducted in a 37° C. rotating culture apparatus for 12 hours. Thereafter, 50 ml of M9 medium was put in the 250 ml flask, and cultured in a 30° C. culture apparatus to induce the expression with 0.03 mM isopropyl β-D-thiogalactopyranoside (IPTG) at the optical density (OD) of 0.8. At 24 and 48 hours, a part of the culture liquid was extracted to measure the optical density (OD) and pH, and the production of 3-HP was confirmed by high performance liquid chromatography (HPLC).

For 3-HP analysis, an Aminex HPX-87H (300 mm*7.8 mm) column was used, and a solution containing 9% acetonitrile in a 0.5 mM sulfuric acid solution was used as a mobile phase and flowed at a flow rate of 0.4 ml/min. The temperature of the column was 35° C., and RI and UV/VIS (210 nm) dual mode was used as a detector. 3-HP was detected at 17.5 minute during the total analysis time of 35 minutes, and the production of 3-HP was also confirmed by Liquid chromatography/mass spectrometry (LC/MS).

Figure 10:
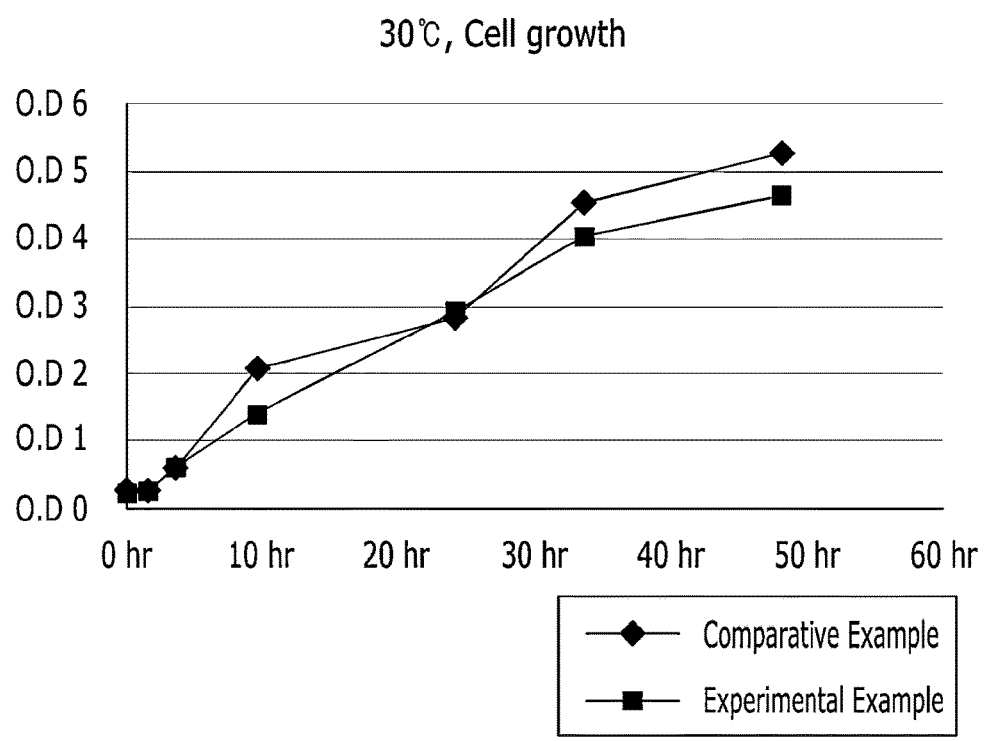
FIG. 10 shows the change in the concentration (OD) of cell culture fluid over time, in the production experiment of 3-HP using the recombinant *E. coli* constructed in Example 1 and Comparative Example 1, under culture condition of 30° C. according to Experimental Example 1.
Figure 11:
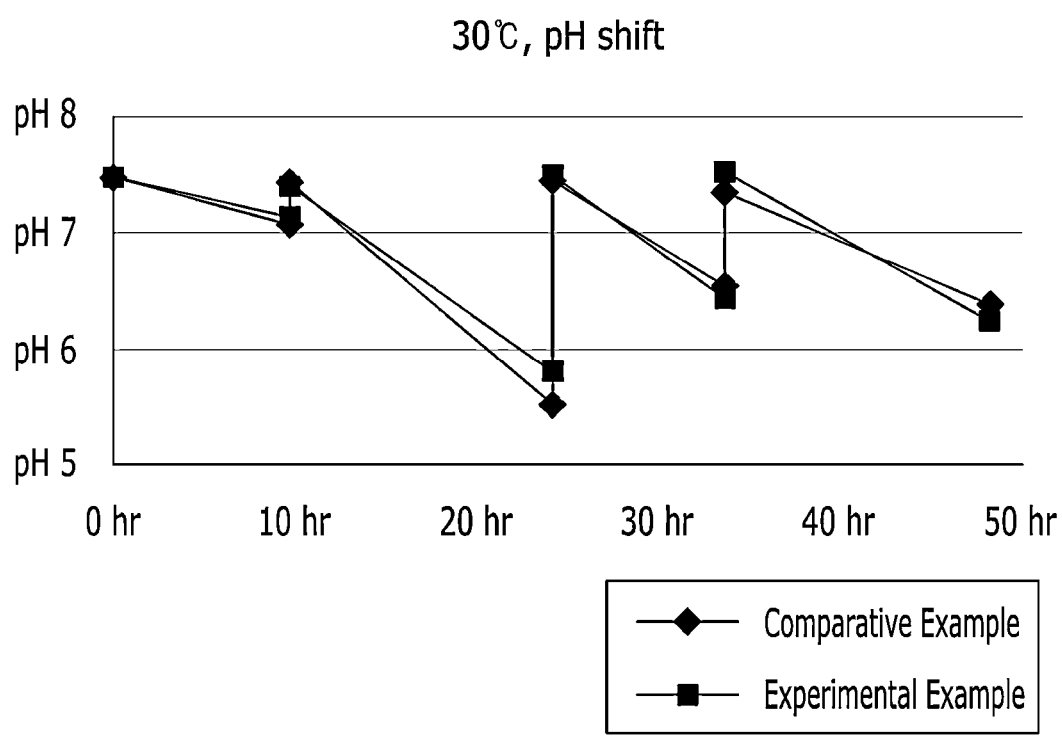
FIG. 11 shows the change in pH of cell culture fluid over time, in the production experiment of 3-HP using the recombinant *E. coli* constructed in Example 1 and Comparative Example 1, under culture condition of 30° C. according to Experimental Example 1.

As shown in FIG. 10 and FIG. 11, although OD values were similar in both strains, the strain of Example 1 showed a little lower value than the strain of Comparative Example 1, and the pH of the culture liquid showed a similar aspect.

Figure 12:
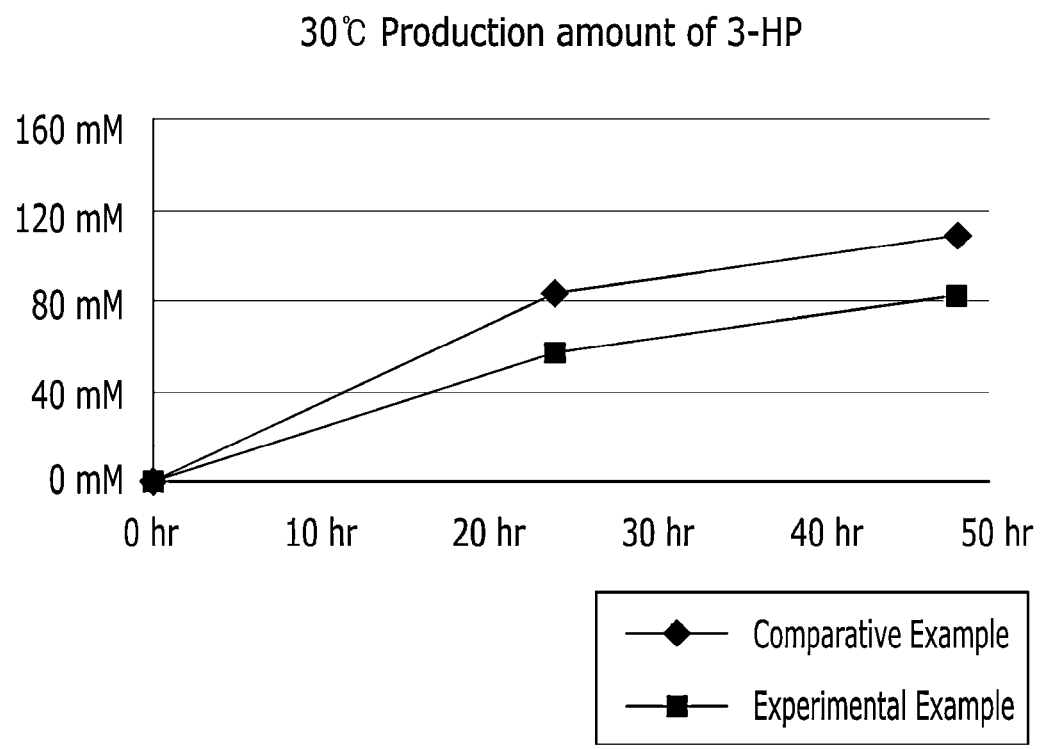
FIG. 12 shows the production amount of 3-HP over time, in the production experiment of 3-HP using the recombinant *E. coli* constructed in Example 1 and Comparative Example 1, under culture condition of 30° C. according to Experimental Example 1.
Figure 13:
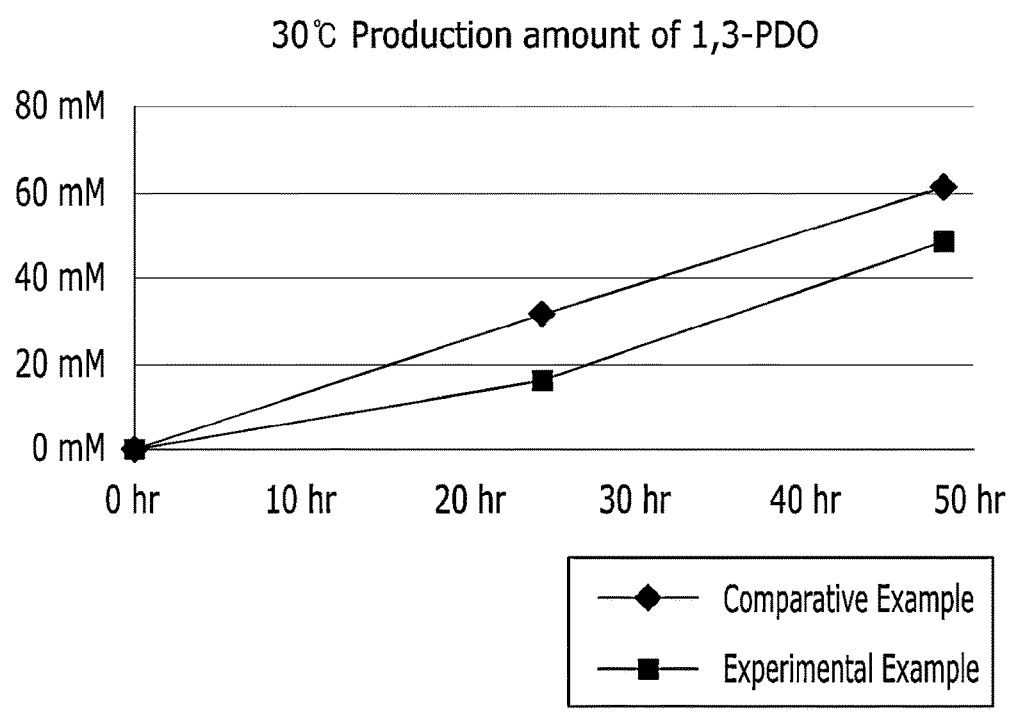
FIG. 13 shows the production amount of 1,3-PDO over time, in the production experiment of 3-HP using the recombinant *E. coli* constructed in Example 1 and Comparative Example 1, under culture condition of 30° C. according to Experimental Example 1.

As to the production amount of 3-HP, the strain of Comparative Example 1 showed 83.72 mM at 24 hours and 109.36 mM at 48 hours at 30° C., while the strain of Example 1 according to the present invention showed 58.27 mM at 24 hours and 83.34 Mm at 48 hours at 30° C. (FIG. 12). As to the production amount of 1,3-PDO, the strain of Comparative Example 1 showed 31.65 Mm at 24 hours and 61.47 mM at 48 hours at 30° C., while strain of Example 1 according to the present invention showed 16.34 mM at 24 hours and 48.89 mM at 48 hours at 30° C. (See FIG. 13).

Figure 14:
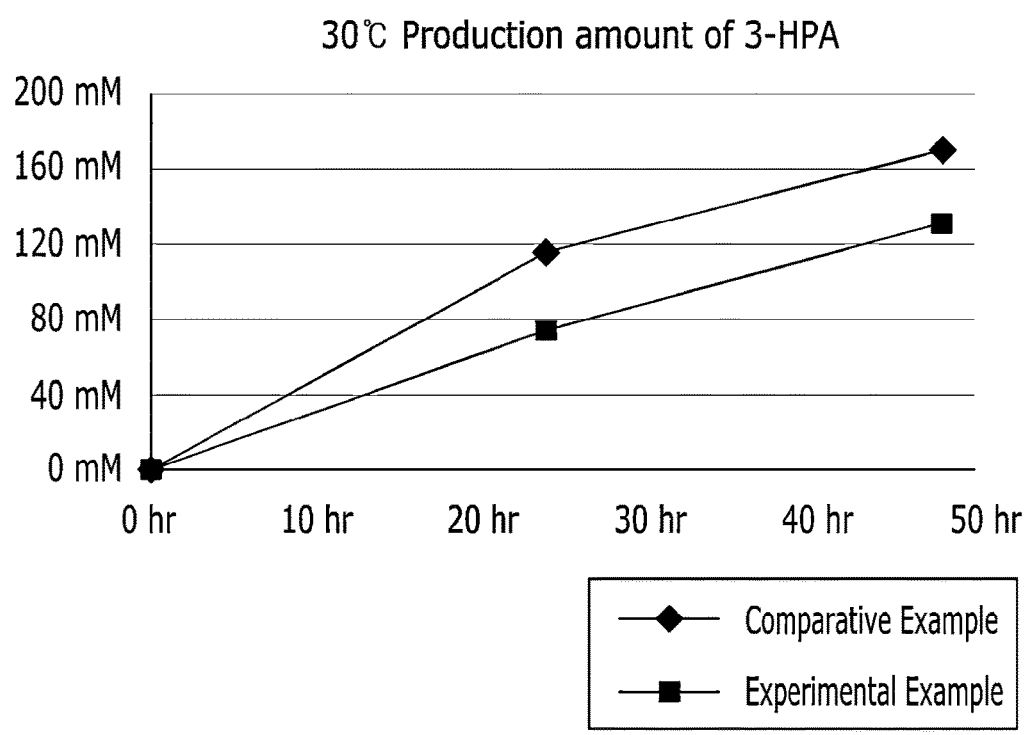
FIG. 14 shows the production amount of 3-HPA over time, in the production experiment of 3-HP using the recombinant *E. coli* constructed in Example 1 and Comparative Example 1, under culture condition of 30° C. according to Experimental Example 1.

As to the production amount of 3-HPA that can be confirmed by adding 3-HP and 1,3-PDO, the strain of Comparative Example 1 showed 116.37 mM at 24 hours and 170.83 mm at 48 hours at 30° C., while the strain of Example 1 according to the present invention showed 74.61 Mm at 24 hours and 132.23 mM at 48 hours at 30° C. (FIG. 14).

As shown in the above experimental results, although the activity of *K. pneumoniae*-derived glycerol dehydratase is superior at a culture temperature of 30° C., it rapidly loses the activity as the temperature increases. To the contrary, *Ilyobacter polytropus*-derived glycerol dehydratase maintains the activity though the temperature increases. Thus, it can be seen that *Ilyobacter polytropus*-derived glycerol dehydratase has superior heat stability to *K. pneumoniae*-derived glycerol dehydratase.

Therefore, it was confirmed that in case *Ilyobacter polytropus*-derived glycerol dehydratase is used according to the present invention, the production amount of 3-HPA increases and thus the production amount of 3-HP increases, compared to the case of using the existing *klebsiella pneumonia*-derived glycerol dehydratase. Furthermore, the generation of by-product 1,3-PDo decreases, and thus, it can be seen that the present invention may increase the production of 3-HP and decrease the generation of 1,3-PDO thus maximizing the production of 3-HP.

Although specific embodiments of the invention have been described in detail, it would be obvious to one of ordinary knowledge in the art that these are no more than preferable embodiments, and the scope of the invention is not limited thereto. Thus, the substantial scope of the invention is defined by the attached claims and equivalents thereof.

The invention claimed is:

1. A method of producing 3-hydroxypropionic acid comprising culturing a recombinant microorganism comprising a nucleic acid encoding an *Ilyobacter polytropus* glycerol dehydratase, and a nucleic acid comprising a *Homo sapiens* gene, an *S. cerevisiae* gene, or an *E. coli* gene encoding a 3-hydroxypropionaldehyde dehydrogenase, which converts 3-hydroxypropionaldehyde into 3-hydroxypropionic acid, with a carbon source to produce 3-hydroxypropionic acid.

2. The method of producing 3-hydroxypropionic acid according to claim 1, wherein the glycerol dehydratase comprises SEQ ID NO: 2, SEQ ID NO: 4, and SEQ ID NO: 6.

3. The method of producing 3-hydroxypropionic acid according to claim 2, wherein the nucleic acid encoding the glycerol dehydratase comprises SEQ ID NO: 1, SEQ ID NO: 3, and SEQ ID NO: 5.

4. The method of producing 3-hydroxypropionic acid according to claim 1, wherein the nucleic acid encoding the 3-hydroxypropionaldehyde dehydrogenase comprises a *Homo sapiens* aldH2 gene, an *S. cerevisiae* ald4 gene, or an *E. coli* aldA, aldB, or aldH gene.

5. The method of producing 3-hydroxypropionic acid according to claim 1, wherein the 3-hydroxypropionaldehyde dehydrogenase comprises SEQ ID NO: 12.

6. The method of producing 3-hydroxypropionic acid according to claim 4, wherein the nucleic acid encoding 3-hydroxypropionaldehyde dehydrogenase comprises a *Homo sapiens* aldH2 gene, an *S. cerevisiae* ald4 gene, or SEQ ID NO: 11.

7. The method of producing 3-hydroxypropionic acid according to claim 1, wherein the recombinant microorganism further comprises a nucleic acid encoding a glycerol dehydratase reactivator, wherein the glycerol dehydratase reactivator is a polypeptide comprising the amino acid sequence of GenBank accession nos. ABI36568.1, EF077655.1, or AAC15871, or comprising SEQ ID NO: 8 and SEQ ID NO: 10.

8. The method of producing 3-hydroxypropionic acid according to claim 7, wherein the nucleic acid encoding a glycerol dehydratase reactivator comprises SEQ ID NO: 7 and SEQ ID NO: 9.

9. The method of producing 3-hydroxypropionic acid according to claim 1, wherein the recombinant microorganism is cultured at a culture temperature of 30° C. or more.

10. An expression cassette comprising a transcription promoter operably linked to a nucleic acid encoding a glycerol dehydratase, a nucleic acid encoding a glycerol dehydratase reactivator, and a transcription terminator,
wherein the glycerol dehydratase comprises SEQ ID NO: 2, SEQ ID NO: 4, and SEQ ID NO: 6, and
the glycerol dehydratase reactivator is a polypeptide comprising SEQ ID NO: 8 and SEQ ID NO: 10.

11. The expression cassette according to claim 10, wherein the nucleic acid encoding the glycerol dehydratase comprises SEQ ID NO: 1, SEQ ID NO: 3, and SEQ ID NO: 5.

12. The expression cassette according to claim 10, further comprising a nucleic acid encoding a 3-hydroxypropionaldehyde dehydrogenase, which comprises a *Homo sapiens* aldH2 gene, an *S. cerevisiae* ald4 gene, or SEQ ID NO: 11.

13. The expression cassette according to claim 10, wherein the nucleic acid encoding a glycerol dehydratase reactivator comprises SEQ ID NO: 7 and SEQ ID NO: 9.

14. A recombinant microorganism comprising the expression cassette according to claim 10.

15. The recombinant microorganism according to claim 14, wherein the nucleic acid sequence encoding glycerol dehydratase comprises SEQ ID NO: 1, SEQ ID NO: 3, and SEQ ID NO: 5.

16. The recombinant microorganism according to claim 14, wherein the expression cassette further comprises a nucleic acid encoding the 3-hydroxypropionaldehyde dehydrogenase, which comprises a *Homo sapiens* aldH2 gene, an *S. cerevisiae* ald4 gene, or SEQ ID NO: 11.

17. The recombinant microorganism according to claim 14, wherein the nucleic acid encoding a glycerol dehydratase reactivator comprises SEQ ID NO: 7 and SEQ ID NO: 9.

18. A recombinant microorganism comprising a nucleic acid encoding an Ilyobacter polytropus glycerol dehydratase, and a nucleic acid comprising a *Homo sapiens* gene, an *S. cerevisiae* gene, or an *E. coli* gene encoding a 3-hydroxypropionaldehyde dehydrogenase, which converts 3-hydroxypropionaldehyde into 3-hydroxypropionic acid.

19. The recombinant microorganism of claim 18, further comprising a nucleic acid encoding a glycerol dehydratase reactivator polypeptide comprising SEQ ID NO: 8 and SEQ ID NO: 10.

* * * * *